US011534192B2

(12) United States Patent
Goldfarb et al.

(10) Patent No.: US 11,534,192 B2
(45) Date of Patent: Dec. 27, 2022

(54) METHODS AND APPARATUS FOR TREATING DISORDERS OF THE SINUSES

(71) Applicant: Acclarent, Inc., Irvine, CA (US)

(72) Inventors: Eric Goldfarb, Belmont, CA (US); Mina W. B. Chow, Campbell, CA (US); John W. White, Menlo Park, CA (US); John Y. Chang, Los Altos, CA (US); Mei Pader, Fremont, CA (US); Jessica M. Liberatore, San Mateo, CA (US); Radit Tantisira, Menlo Park, CA (US); Serena Swei Loh, San Carlos, CA (US); Josh Makower, Los Altos, CA (US); Hung Vo, Sunnyvale, CA (US); Isidro M. Gandionco, Fremont, CA (US); Michael J. Gottesman, Redwood City, CA (US)

(73) Assignee: Acclarent, Inc., Irvine, CA (US)

( * ) Notice: Subject to any disclaimer, the term of this patent is extended or adjusted under 35 U.S.C. 154(b) by 197 days.

(21) Appl. No.: 16/017,925

(22) Filed: Jun. 25, 2018

(65) Prior Publication Data
US 2018/0296236 A1 Oct. 18, 2018

Related U.S. Application Data

(63) Continuation of application No. 13/222,414, filed on Aug. 31, 2011, now abandoned.
(Continued)

(51) Int. Cl.
*A61B 17/24* (2006.01)
*A61M 25/01* (2006.01)
(Continued)

(52) U.S. Cl.
CPC ......... *A61B 17/24* (2013.01); *A61M 25/0113* (2013.01); *A61M 25/09041* (2013.01);
(Continued)

(58) Field of Classification Search
CPC .............. A61B 17/24; A61B 2017/246; A61B 2017/2929; A61M 25/0013;
(Continued)

(56) References Cited

U.S. PATENT DOCUMENTS 5,137,288 A * 8/1992 Starkey ................. A61M 25/09
279/42
5,161,534 A * 11/1992 Berthiaume .......... A61M 25/01
226/127
(Continued)

FOREIGN PATENT DOCUMENTS

| CN | 101553190 | 10/2009 |
| RU | 2213530 | 10/2003 |

(Continued)

OTHER PUBLICATIONS

State Intellectual Property Office of People's Republic China, Search Report, dated Jan. 27, 2015, 2 pgs.
(Continued)

*Primary Examiner* — Diane D Yabut
*Assistant Examiner* — Christian D Knauss
(74) *Attorney, Agent, or Firm* — Frost Brown Todd LLC

(57) ABSTRACT

A medical device for the treatment of a sinus opening includes a handle, a grooming sheath, a rail, a guide wire, a balloon catheter and a balloon catheter movement mechanism. The handle has a proximal end, a distal end and a longitudinal axis along the length of the handle. The grooming sheath has a distal end and a proximal end with the proximal end of the grooming sheath being attached to the
(Continued)

distal end of the handle. The rail has a distal end and a proximal end and disposed partially within the grooming sheath to define an annular lumen is between the rail and the grooming sheath. The guide wire operatively extends from the distal end of the rail and the balloon catheter is disposed at least partially in the handle and annular lumen. The balloon catheter movement mechanism operatively disposed on the handle and configured for advancement and retraction of the balloon catheter through both the handle and the annular lumen and along both the rail and guide wire by user operation of the balloon catheter movement mechanism. A method for treating a sinus opening includes inserting a medical device for the treatment of a sinus opening partially into a patient's anatomy and then positioning a guide wire operatively extending from a rail of a medical device into a sinus opening of the patient. The method further includes advancing a balloon catheter from an annular lumen of the medical device and along both the rail of the medical device and the guide wire. The method also includes treating the sinus opening via inflation of the balloon catheter. In the method, the annular lumen is between the rail and a grooming sheath of the medical device and the advancing is accomplished via user operation of a balloon catheter movement mechanism of the medical device.

20 Claims, 30 Drawing Sheets

Related U.S. Application Data

(60) Provisional application No. 61/511,237, filed on Jul. 25, 2011, provisional application No. 61/511,290, filed on Jul. 25, 2011, provisional application No. 61/385,591, filed on Sep. 23, 2010, provisional application No. 61/385,263, filed on Sep. 22, 2010, provisional application No. 61/385,250, filed on Sep. 22, 2010.

(51) Int. Cl.
| | |
|---|---|
| *A61M 25/09* | (2006.01) |
| *A61B 1/00* | (2006.01) |
| *A61B 17/32* | (2006.01) |
| *A61B 17/3207* | (2006.01) |
| *A61B 17/00* | (2006.01) |
| *A61B 17/22* | (2006.01) |
| *A61M 29/02* | (2006.01) |
| *A61M 25/06* | (2006.01) |

(52) U.S. Cl.
CPC ....... *A61B 1/00147* (2013.01); *A61B 17/3207* (2013.01); *A61B 17/320016* (2013.01); *A61B 2017/00331* (2013.01); *A61B 2017/22042* (2013.01); *A61B 2017/22069* (2013.01); *A61M 29/02* (2013.01); *A61M 2025/0681* (2013.01); *A61M 2025/09125* (2013.01)

(58) Field of Classification Search
CPC .. A61M 25/09041; A61M 2025/09125; A61M 2210/0681; A61M 25/0136; A61M 2025/09116

See application file for complete search history.

(56) References Cited

U.S. PATENT DOCUMENTS

| | | | |
|---|---|---|---|
| 5,344,428 A | | 9/1994 | Griffiths |
| 5,392,778 A | * | 2/1995 | Horzewski ...... A61M 25/09041 |
| | | | 600/434 |
| 6,027,478 A | | 2/2000 | Katz |
| 6,645,222 B1 | * | 11/2003 | Parodi ..................... A61F 2/013 |
| | | | 606/200 |
| 7,462,172 B2 | | 12/2008 | Wright et al. |
| 7,462,175 B2 | | 12/2008 | Chang et al. |
| 7,500,971 B2 | | 3/2009 | Chang et al. |
| 7,645,272 B2 | | 1/2010 | Chang et al. |
| 7,654,997 B2 | | 4/2010 | Makower et al. |
| 7,803,150 B2 | | 9/2010 | Chang et al. |
| 2006/0063973 A1 | | 3/2006 | Makower |
| 2006/0095066 A1 | | 5/2006 | Chang et al. |
| 2007/0112358 A1 | | 5/2007 | Abbott et al. |
| 2007/0129751 A1 | | 6/2007 | Muni et al. |
| 2007/0167682 A1 | * | 7/2007 | Goldfarb ............ A61B 1/00154 |
| | | | 600/114 |
| 2007/0250105 A1 | | 10/2007 | Ressemann |
| 2008/0015544 A1 | | 1/2008 | Keith et al. |
| 2008/0097154 A1 | * | 4/2008 | Makower ........... A61B 1/00135 |
| | | | 600/114 |
| 2008/0097515 A1 | | 4/2008 | Chang et al. |
| 2008/0119693 A1 | * | 5/2008 | Makower ................ A61B 1/018 |
| | | | 600/114 |
| 2008/0195041 A1 | | 8/2008 | Goldfarb |
| 2008/0228085 A1 | | 9/2008 | Jenkins et al. |
| 2008/0234720 A1 | | 9/2008 | Chang et al. |
| 2008/0275483 A1 | | 11/2008 | Makower et al. |
| 2008/0281156 A1 | | 11/2008 | Makower et al. |
| 2008/0287908 A1 | | 11/2008 | Muni et al. |
| 2009/0093823 A1 | | 4/2009 | Chang et al. |
| 2009/0198216 A1 | | 8/2009 | Muni et al. |
| 2009/0312745 A1 | * | 12/2009 | Goldfarb ................ A61M 25/09 |
| | | | 604/514 |
| 2010/0030113 A1 | * | 2/2010 | Morriss .................. A61M 29/00 |
| | | | 600/585 |
| 2010/0099946 A1 | * | 4/2010 | Jenkins .................. A61B 17/24 |
| | | | 600/104 |
| 2010/0312101 A1 | * | 12/2010 | Drontle .................. A61B 17/24 |
| | | | 600/424 |
| 2010/0312338 A1 | | 12/2010 | Gonzales |

FOREIGN PATENT DOCUMENTS

| | | |
|---|---|---|
| WO | WO 2006/135853 | 12/2006 |
| WO | WO 2010/033629 | 3/2010 |
| WO | WO 2010/078145 | 7/2010 |

OTHER PUBLICATIONS

International Searching Authority (ISA), Written Opinion of the ISA International Preliminary Report on Patentability, International Application No. PCT/US2011/049929, dated Nov. 15, 2011, 8 pgs.
International Bureau of WIPI, Written Opinion of the ISA, International Application No. PCT/US2011/049929, 8 pgs.
International Search Report re: PCT/US2011/049929 dated Nov. 15, 2011.

* cited by examiner

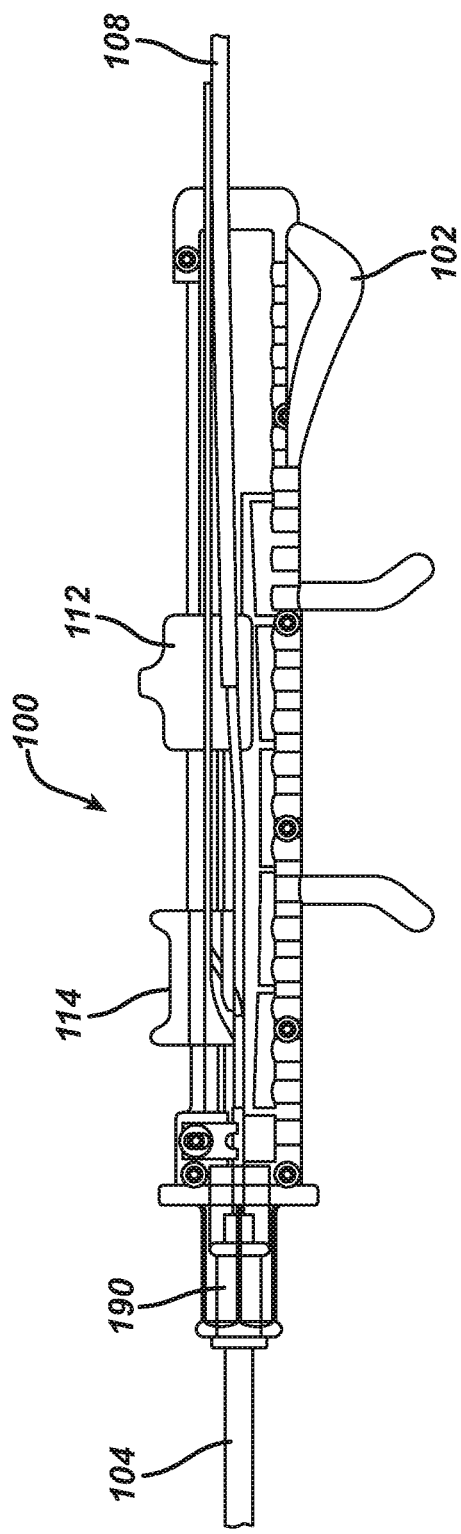

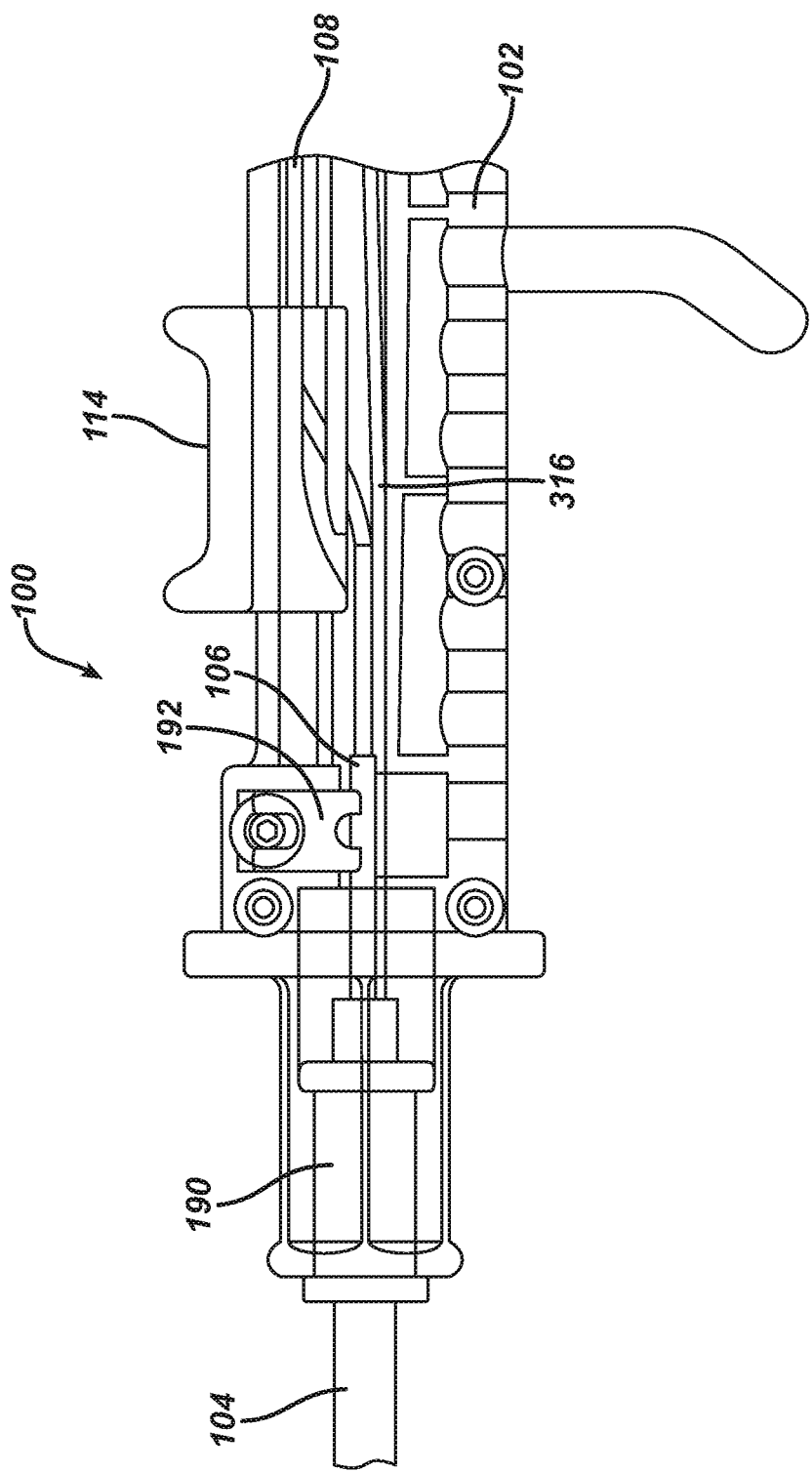

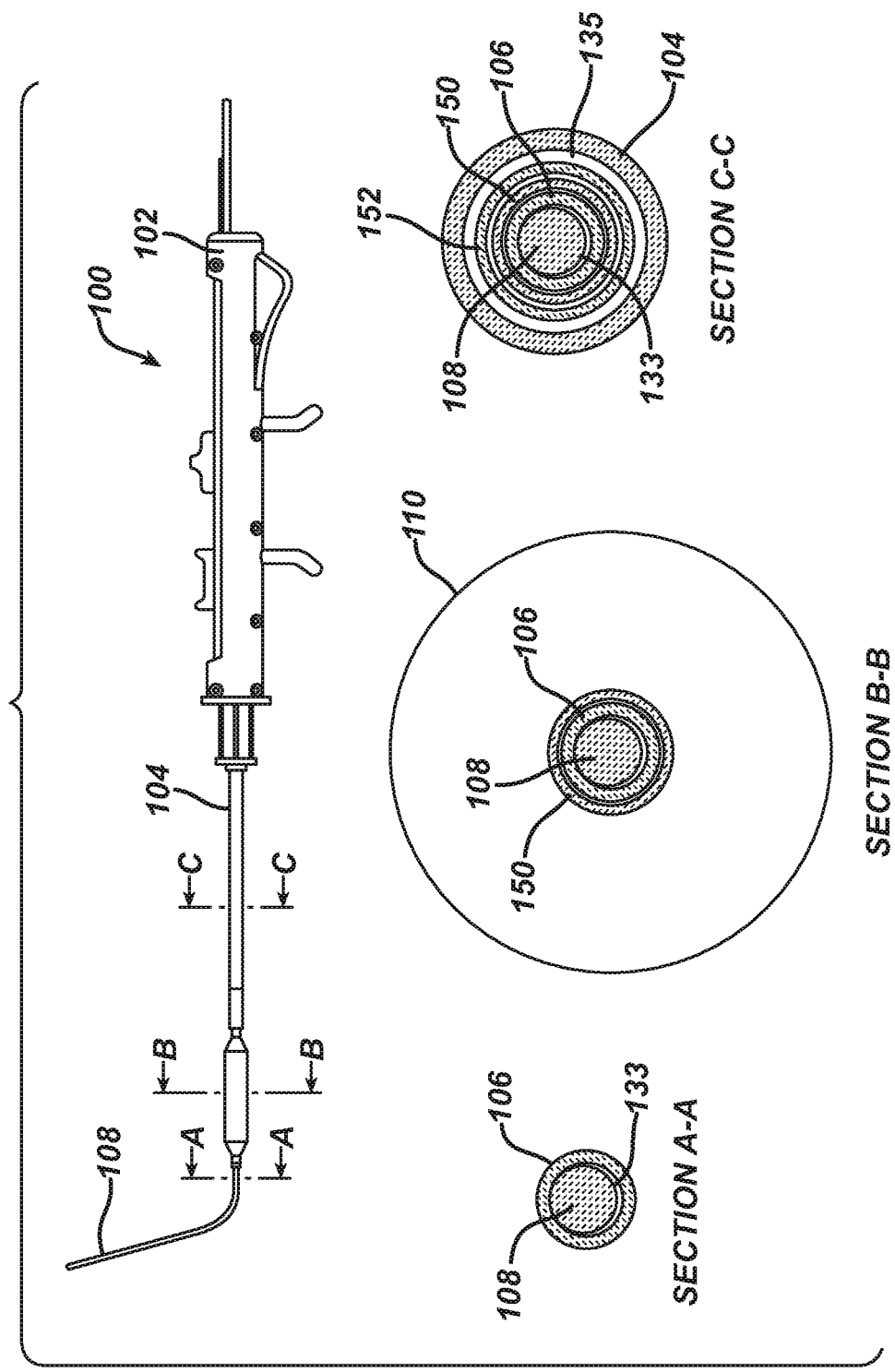

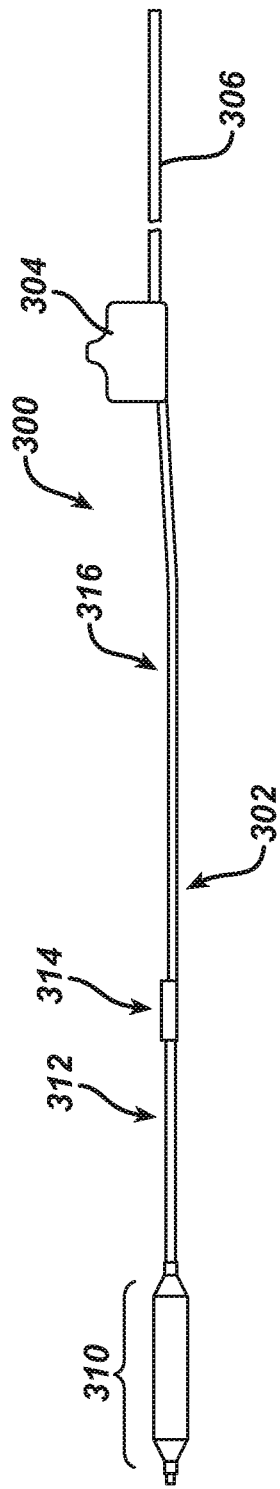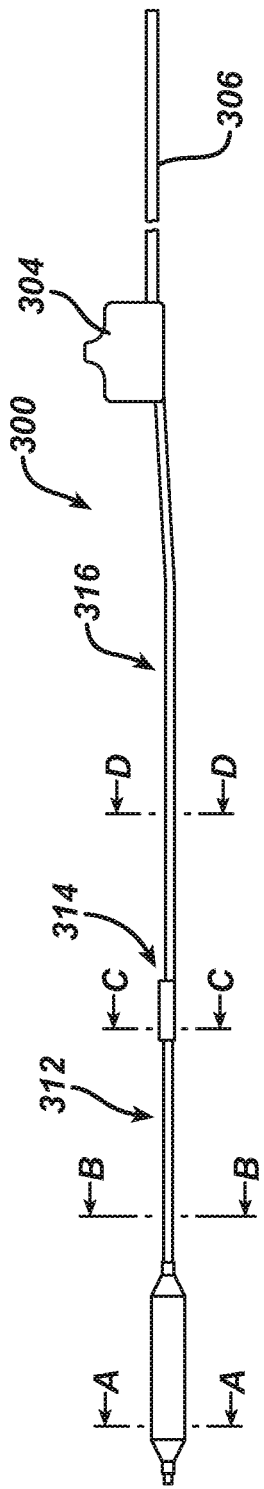

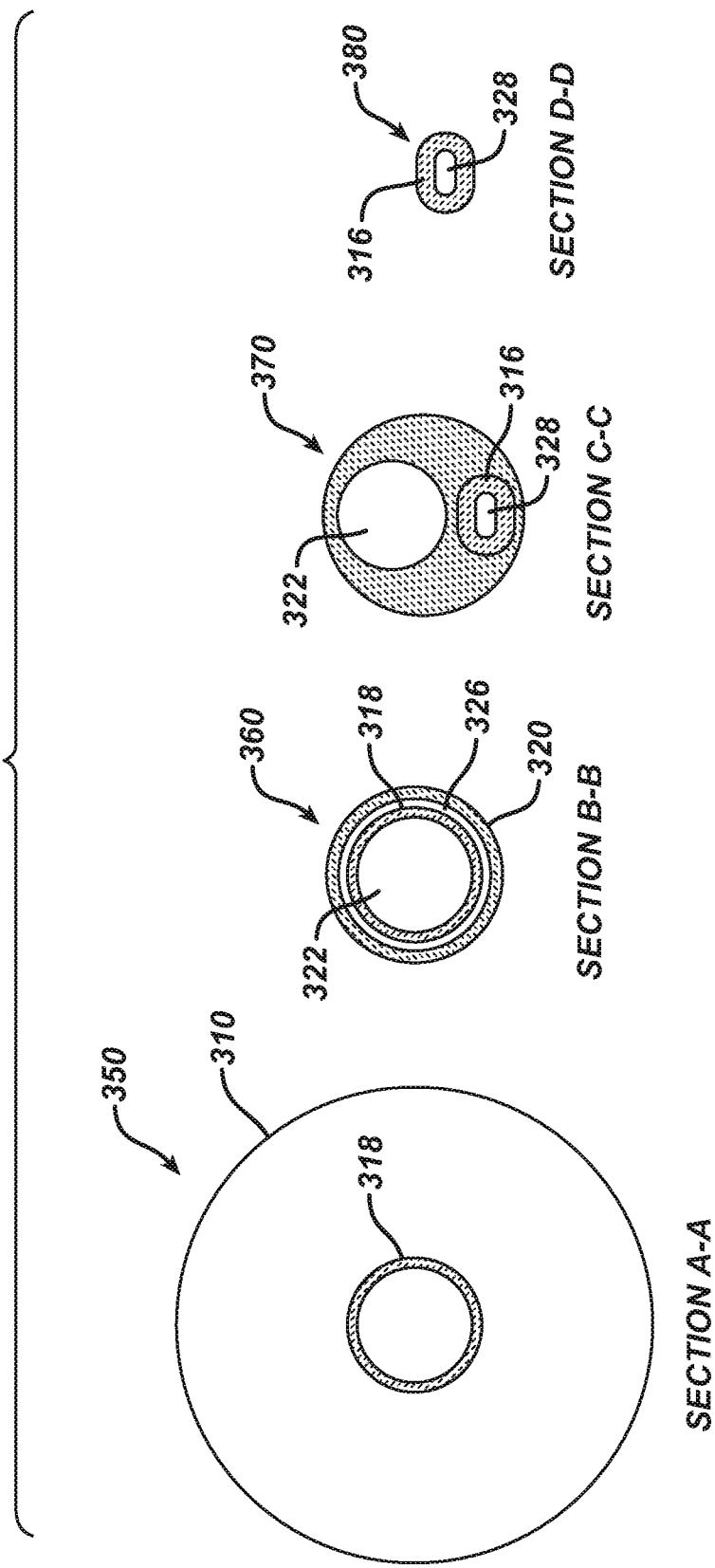

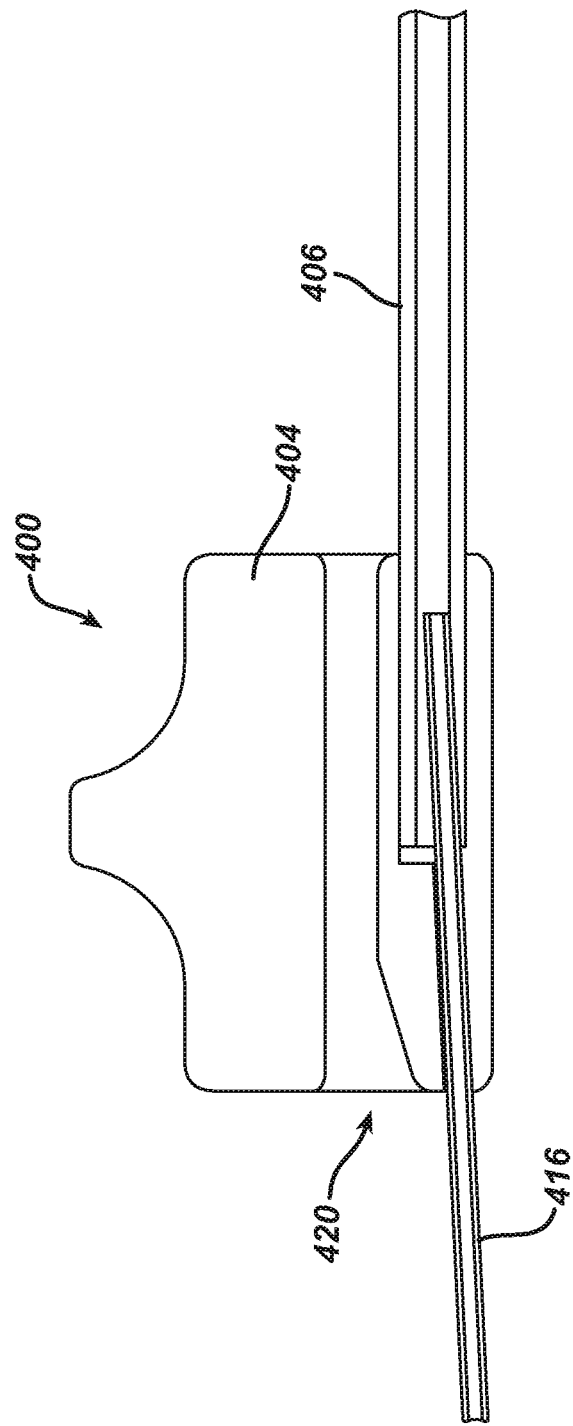

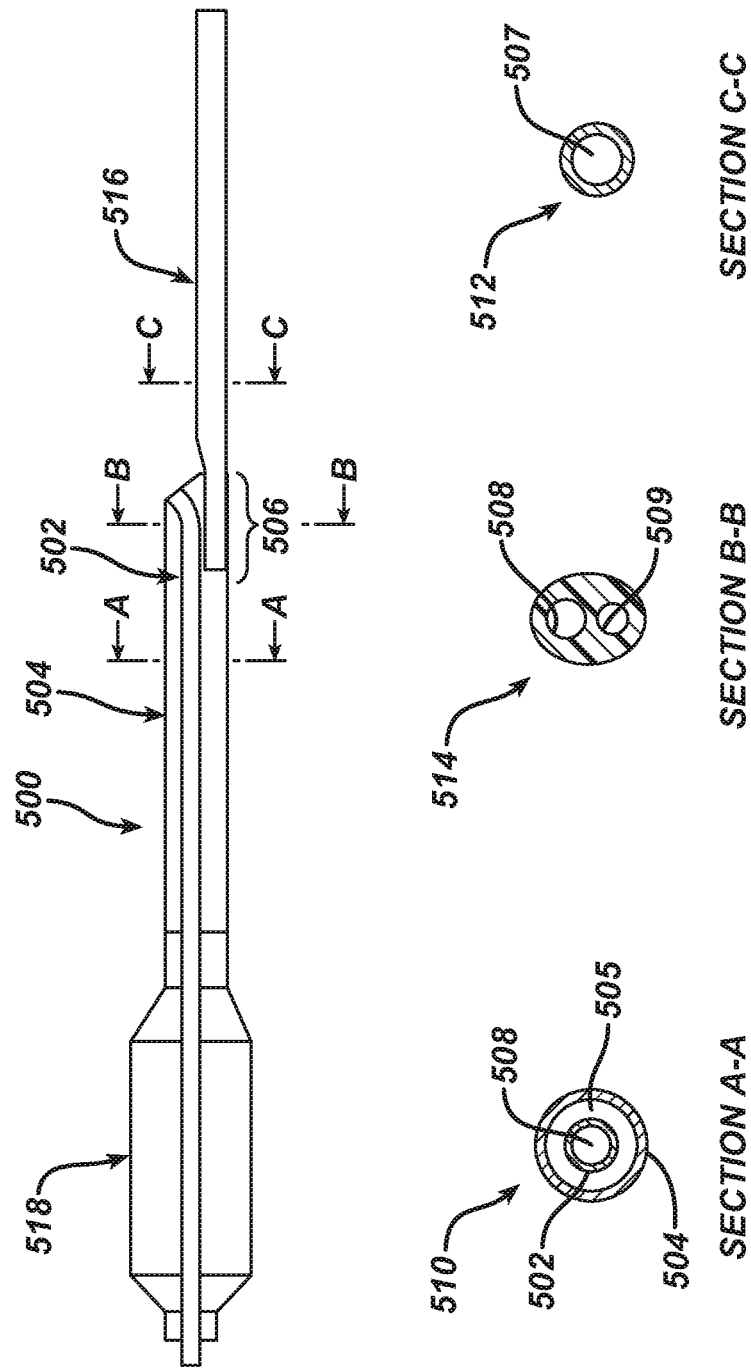

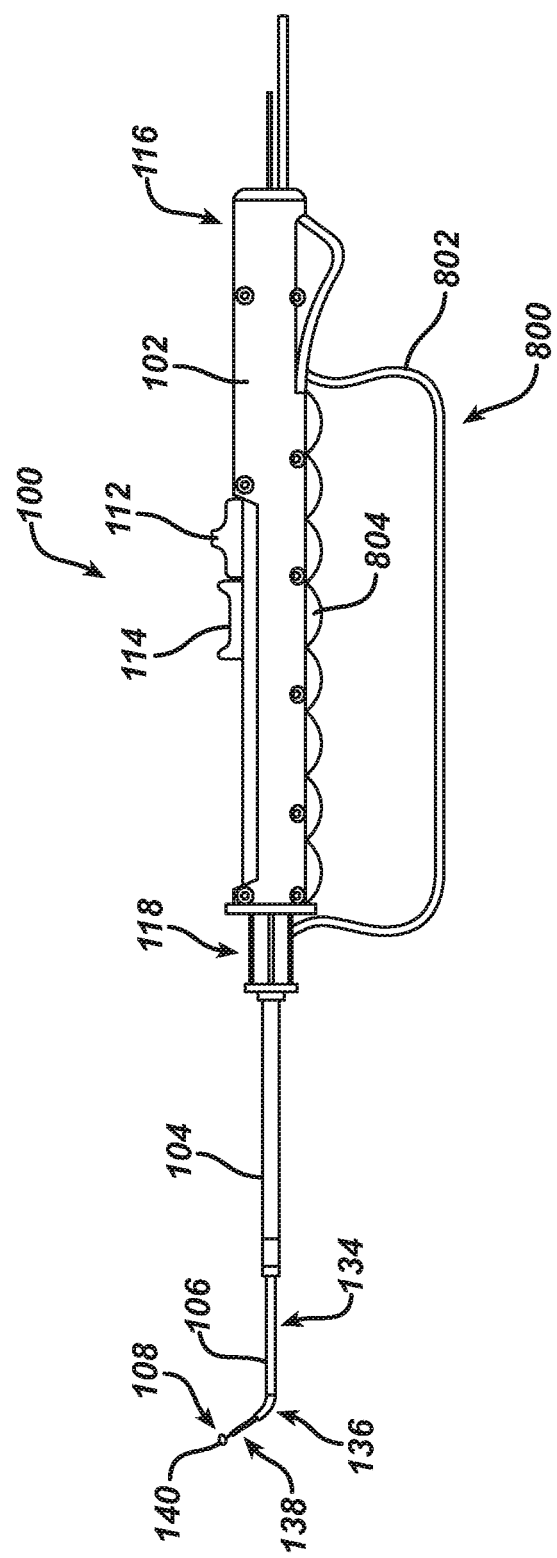

METHODS AND APPARATUS FOR TREATING DISORDERS OF THE SINUSES

RELATED APPLICATIONS

This application is a continuation of U.S. Non-provisional application Ser. No. 13/222,414 filed Aug. 31, 2011, now abandoned, entitled "Methods and Apparatus for Treating Disorders of the Sinuses", which claims priority pursuant to 35 U.S.C. § 119 to U.S. Provisional Patent Application Ser. No. 61/385,250, entitled "Medical Device for Treatment of a Sinus Opening" filed on Sep. 22, 2010, to U.S. Provisional Patent Application Ser. No. 61/385,263, entitled "Method for Treating a Sinus Opening" filed on Sep. 22, 2010, to U.S. Provisional Patent Application Ser. No. 61/385,591, entitled "Methods and Apparatus for Treating Disorders of the Ear, Nose and Throat" filed on Sep. 23, 2010, to U.S. Provisional Patent Application Ser. No. 61/511,237, entitled "Medical Device and Method for Treatment of a Sinus Opening" filed on Jul. 25, 2011, and U.S. Provisional Patent Application Ser. No. 61/511,290, entitled "Methods and Apparatus for Treating Disorders of the Sinuses" filed on Jul. 25, 2011, the entirety of these applications being incorporated herein by reference thereto.

FIELD OF THE INVENTION

The present invention relates, in general, to medical devices and, in particular, to medical devices and related methods for the treatment of sinus conditions.

BACKGROUND OF THE INVENTION

The paranasal sinuses are hollow cavities in the skull connected by small openings, known as ostia, to the nasal canal. Each ostium between a paranasal sinus and the nasal cavity is formed by a bone covered by a layer of mucosal tissue. Normally, air passes into and out of the paranasal sinuses through the ostia. Also, mucus is continually formed by the mucosal lining of the sinuses and drains through the ostia and into the nasal canal.

Sinusitis is a general term that refers to inflammation in one or more of the paranasal sinuses. Acute sinusitis can be associated with upper respiratory infections or allergic conditions, which may cause tissue swelling and temporarily impede normal trans-ostial drainage and ventilation of the sinuses, thereby resulting in some collection of mucus and possibly infection within the sinus cavities. Chronic sinusitis is a long term condition characterized by persistent narrowing or blockage of one or more sinus ostia, resulting in chronic infection and inflammation of the sinuses. Chronic sinusitis is often associated with longstanding respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than one genus of micro-organism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

The most common surgical procedure for treating chronic sinusitis is functional endoscopic sinus surgery (FESS). FESS is commonly performed using an endoscope and various rigid instruments inserted through the patient's nostril. The endoscope is used to visualize the positioning and use of various rigid instruments used for removing tissue from the nasal cavity and sinus ostia in an attempt to improve sinus drainage.

A technique known as the Balloon Sinuplasty™ procedure and a system for performing the procedure has been developed by Acclarent Inc, of Menlo Park, Calif. for treatment of sinusitis. A number of US patents and patent applications including U.S. Pat. Nos. 7,645,272, 7,654,997, and 7,803,150 and Publications 2008/0097154, issued as U.S. Pat. No. 8,080,000 on Dec. 20, 2011, and 2008/0281156, issued as U.S. Pat. No. 9,167,961 on Oct. 27, 2015, each of which is hereby incorporated in full by reference, describe various embodiments of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into the affected paranasal sinus. Thereafter, a dilation catheter having an expandable dilator (e.g. an inflatable balloon) is advanced over the guidewire to a position where the dilator is positioned within the ostium of the affected paranasal sinus. The dilator is then expanded, causing dilation of the ostium and remodelling of bone adjacent to the ostium, without required incision of the mucosa or removal of any bone. The catheters and guidewire are then removed and the dilated ostium allows for improved drainage from and ventilation of the affected paranasal sinus. There is a continuing need for improved methods and devices for treating the paranasal sinus.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements.

BRIEF DESCRIPTION OF THE DRAWINGS

FIG. 10 is a simplified side cross-sectional depiction of a portion of the medical device of FIG. 8;

FIG. 11 is another simplified side cross-sectional depiction of a portion of the medical device of FIG. 8;

FIG. 12 is a combined side view and multi-cross-sectional view of the medical device of FIG. 3;

FIG. 13 is a simplified depiction of a balloon catheter sub-assembly as can be employed in embodiments of the present invention;

FIGS. 14A and 14B are simplified side and cross-sectional views of the balloon catheter sub-assembly of FIG. 13;

FIG. 16 is a simplified cross-sectional view of a portion of the balloon catheter sub-assembly of FIG. 15;

FIG. 17A and 17B are combined side views and multi-cross-sectional views of balloon catheters as can be employed in embodiments of the present invention.

FIG. 18 is an embodiment of the device according to the invention showing a side view of an alternative handle design.

SUMMARY OF THE INVENTION

Figure 1:
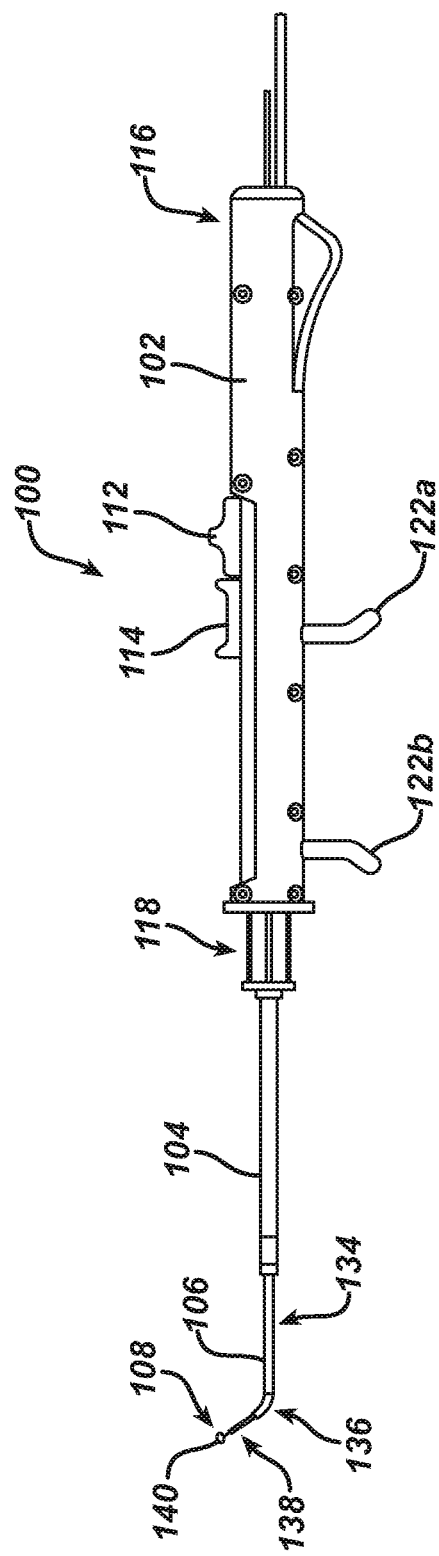
FIG. 1 is a simplified side view depiction of a medical device according to an embodiment of the present invention.

The present invention provides devices and methods for treating a sinus opening.

In one aspect, a medical device is provided for the treatment of a sinus opening. The medical device includes a handle with a proximal end, a distal end, and a longitudinal axis along the length of the handle. The medical device further includes a grooming sheath with a distal end and a proximal end, the proximal end of the grooming sheath attached to the distal end of the handle and a rail with a distal end and a proximal end and disposed partially within the grooming sheath such that an annular lumen is defined between the rail and the grooming sheath, the distal end of the rail having an angled shape with an angle appropriate for a particular sinus, the rail being rotatable relative to the longitudinal axis. The guide wire operatively extends from the distal end of the rail, a balloon catheter is disposed at least partially in the handle and annular lumen, and a balloon catheter movement mechanism is operatively disposed on the handle. The balloon catheter movement mechanism is configured for advancement and retraction of the balloon catheter through the handle and annular lumen and along the rail and guide wire by user operation of the balloon catheter movement mechanism.

In one embodiment, the distal end of the grooming sheath is expandable to facilitate advancement and retraction of the balloon catheter. In a further embodiment, the expandable grooming sheath includes expandable slits.

In another embodiment, the guide wire is attached to the distal end of the rail and extends beyond the distal end of the rail a predetermined fixed length.

In a further embodiment, the medical device includes a guide wire movement mechanism operatively disposed on the handle. The rail has a rail lumen, the guide wire is disposed at least partially in the handle and the rail lumen, and wherein the guide wire movement mechanism and the guide wire are configured for advancement and retraction of the guide wire through the handle and rail lumen by user operation of the guide wire movement mechanism.

In another embodiment the guide medical device includes a guide wire locking and rotation mechanism.

In another embodiment the guide wire has a proximal end, a distal end and an atraumatic tip attached to the guide wire distal end.

In a further embodiment, the grooming sheath is configured to collapse a deflated balloon catheter during retraction of the balloon catheter into the annular lumen.

In another embodiment, the balloon catheter has a working segment. In one embodiment, the working segment has a distal extension. In another embodiment, the balloon catheter, rail and guide wire are configured such that the balloon catheter can be advanced from the annular opening in a manner that the working segment is positioned entirely over the guide wire, partially over the guide wire and partially over the rail, at least partially extended beyond the end of the guide wire for inflation of the balloon catheter.

In a further embodiment at least a portion of the rail is formed of a malleable material such that the shape of the rail can be manipulated by a user.

In another embodiment, the first rail may be removed and replaced with a second rail having a second angled shape.

In still another embodiment the rail includes an endoscopic visible marking.

In another embodiment the distal end of the grooming sheath includes an atraumatic tip.

In another aspect, a method is provided for treating a sinus opening, the method includes inserting a medical device for the treatment of a sinus opening partially into a patient's anatomy, positioning a guide wire operatively extending from a rail of a medical device into a sinus opening of the patient, advancing a balloon catheter of the medical device from an annular lumen of the medical device and along both the rail of the medical device and the guide wire, and treating the sinus opening is accomplished via inflation of the balloon catheter. The annular lumen is between the rail and a grooming sheath of the medical device, and the advancing is accomplished via user operation of a balloon catheter movement mechanism of the medical device.

In a further embodiment, the method includes deflating the balloon catheter, retracting the balloon catheter into the grooming sheath, optionally retracting the guide wire into the rail lumen and removing the medical device from the patient's anatomy.

In another embodiment the positioning includes advancing the guide wire from a rail lumen of the rail via a sliding movement of a guide wire movement mechanism of the medical device along a handle of the medical device.

In another embodiment, the patient's anatomy is a nostril.

In yet a further embodiment, the rail is formed of a malleable material and the method further includes configuring the malleable rail into a shape appropriate for the sinus opening to be treated prior to the inserting step.

In another embodiment, the treating step includes inflating a working segment of the balloon catheter that is disposed entirely over the guide wire, or partially over the guide wire and partially over the rail, or that extends beyond a distal end of the guide wire.

In a further embodiment, the method includes suctioning the sinus opening.

In yet another embodiment, the method includes irrigating the sinus opening.

DETAILED DESCRIPTION

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, medical devices for the treatment of a sinus opening according to embodiments of the present invention include a handle, a grooming sheath, a rail, a guide wire, a balloon catheter and a balloon catheter movement mechanism. The handle has a proximal end, a distal end and a longitudinal axis along the length of the handle, while the grooming sheath has a distal end and a proximal end with the proximal end of the grooming sheath being attached to the distal end of the handle. The rail of medical devices according to embodiments of the present invention has a distal end and a proximal end and is disposed partially within the grooming sheath to define an annular lumen between the rail and the grooming sheath. The guide wire operatively extends from the distal end of the rail and the balloon catheter of the medical device is disposed at least partially in the handle and annular lumen. The balloon catheter movement mechanism of the medical devices is operatively disposed on the handle and configured for advancement and retraction of the balloon catheter through both the handle and the annular lumen and along both the rail and guide wire by user operation of the balloon catheter movement mechanism via, for example, longitudinal sliding of the balloon catheter movement mechanism along the handle.

Medical devices according to embodiments of the present invention are beneficial in that, for example, their configuration provides for a particularly efficient preparation and treatment of a patient's sinus opening and is mechanically simple. Moreover, the simplicity of the medical devices provides for them to be manufactured in a cost effective manner. In addition, the rail of medical devices according to embodiments of the present invention is sufficiently stiff that it can be beneficially employed to seek and access sinus anatomy followed by a convenient advancement and inflation of a balloon catheter there along using, for example, only one hand of the user. The medical devices are also beneficial in that the balloon catheter is advanced over the stiff rail resulting in the balloon catheter being well supported and advancing (tracking) smoothly through the sinus anatomy. Although described with regard to the sinus opening, the inventions described herein may also be useful for the treatment of the Eustachian tube, repair of endo-cranial fractures, airway procedures such as subglottic stenosis dilation and other procedures of the ear, nose or throat.

Figure 2:
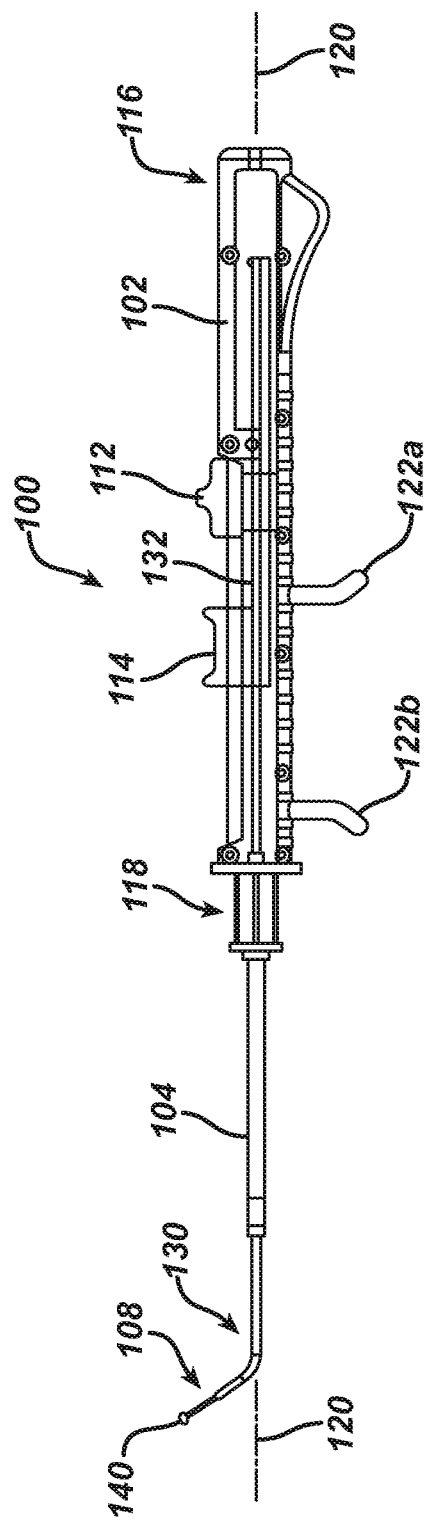
FIG. 2 is a simplified cross-sectional depiction of the medical device of FIG. 1.
Figure 3:
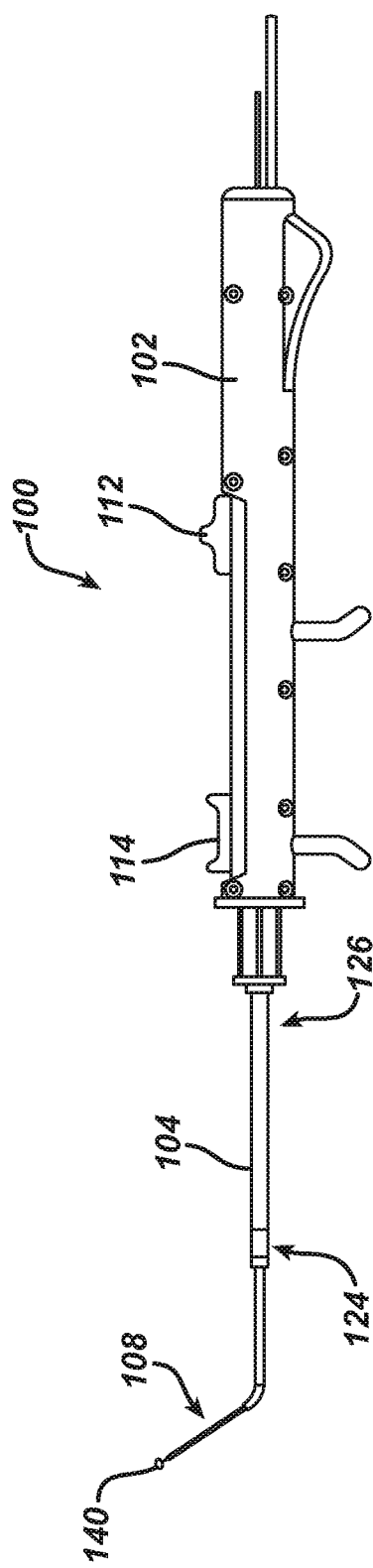
FIG. 3 is a simplified side view of the medical device of FIG. 1 with a guide wire of the medical device extended.
Figure 4:
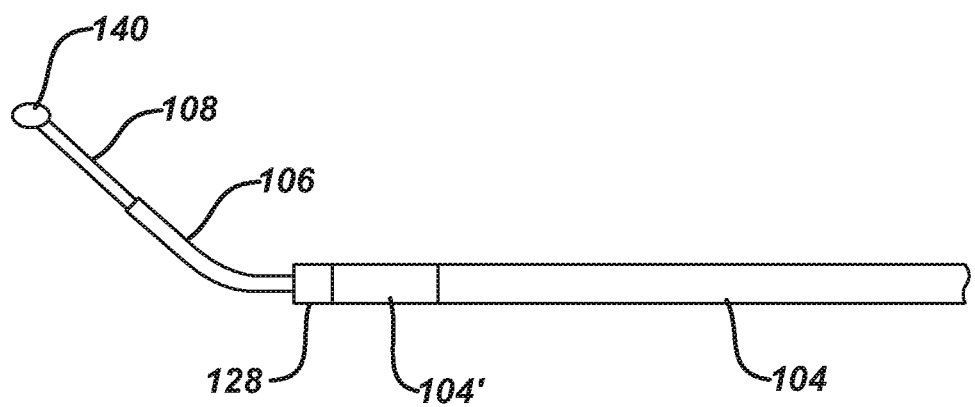
FIG. 4 is a simplified perspective depiction of the guide wire, rail and grooming sheath of the medical device of FIG. 3.
Figure 5:
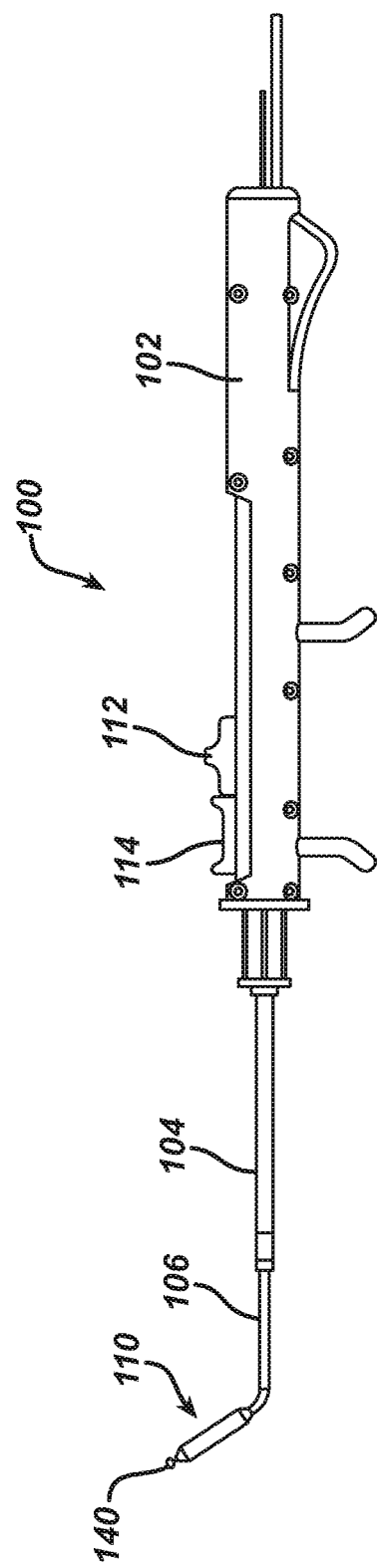
FIG. 5 is a simplified side depiction of the medical device of FIG. 1 with the guide wire and balloon catheter of the medical device extended and the balloon catheter inflated over the guide wire.
Figure 6:
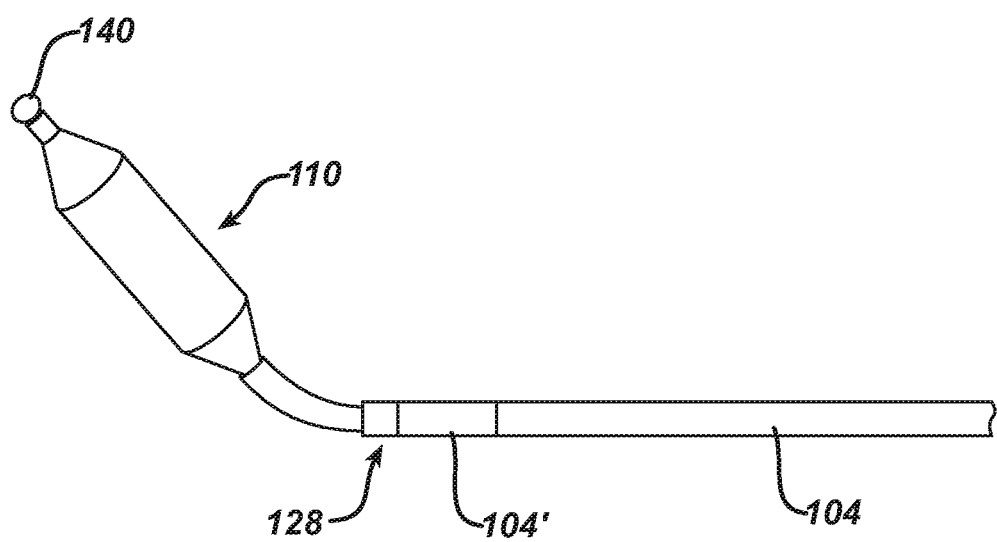
FIG. 6 is a simplified perspective depiction of the guide wire, balloon catheter, and grooming sheath of the medical device of FIG. 5.

FIG. 1 is a simplified side view depiction of a medical device 100 for the treatment of a sinus opening according to an embodiment of the present invention. FIG. 2 is a simplified cross-sectional depiction of medical device 100. FIG. 3 is a simplified side view of the medical device 100 with a guide wire of the medical device extended. FIG. 4 is a simplified perspective depiction of the guide wire, rail and grooming sheath of medical device 100. FIG. 5 is a simplified side depiction of the medical device 100 with the guide wire and balloon catheter of the medical device fully extended and the balloon catheter inflated. FIG. 6 is a simplified perspective depiction of the guide wire, balloon catheter, and grooming sheath of medical device 100.

Referring to FIGS. 1 through 5, medical device 100 includes a handle 102, a grooming sheath 104, a rail 106, a guide wire 108, a balloon catheter 110, a balloon catheter movement mechanism 112 and a guide wire movement mechanism 114.

Handle 102 has a proximal end 116, a distal end 118, a longitudinal axis 120 (the extension of which is marked by dashed lines in FIG. 2 to avoid obscuring other components of the medical device) along the length of handle 102, and finger anchoring pegs 122a and 122b. The anchoring pegs 122a and 122b may be stationary or may be rotatable around the handle for a more comfortable, personsalizable grip.

Handle 102 can be formed of any suitable material including, for example, polycarbonate and ABS (acetonitrile butadiene styrene) and can be manufactured using any suitable technique including, for example, injection molding of two clam shell handle halves. The two clam shell handle halves can be closed using any suitable manufacturing technique including, for example, adhesive bonding, screw fastening, clip-based fastening using clips molded as integral portions of the handle halves, or pins press fitted into the handle halves.

Figure 19:
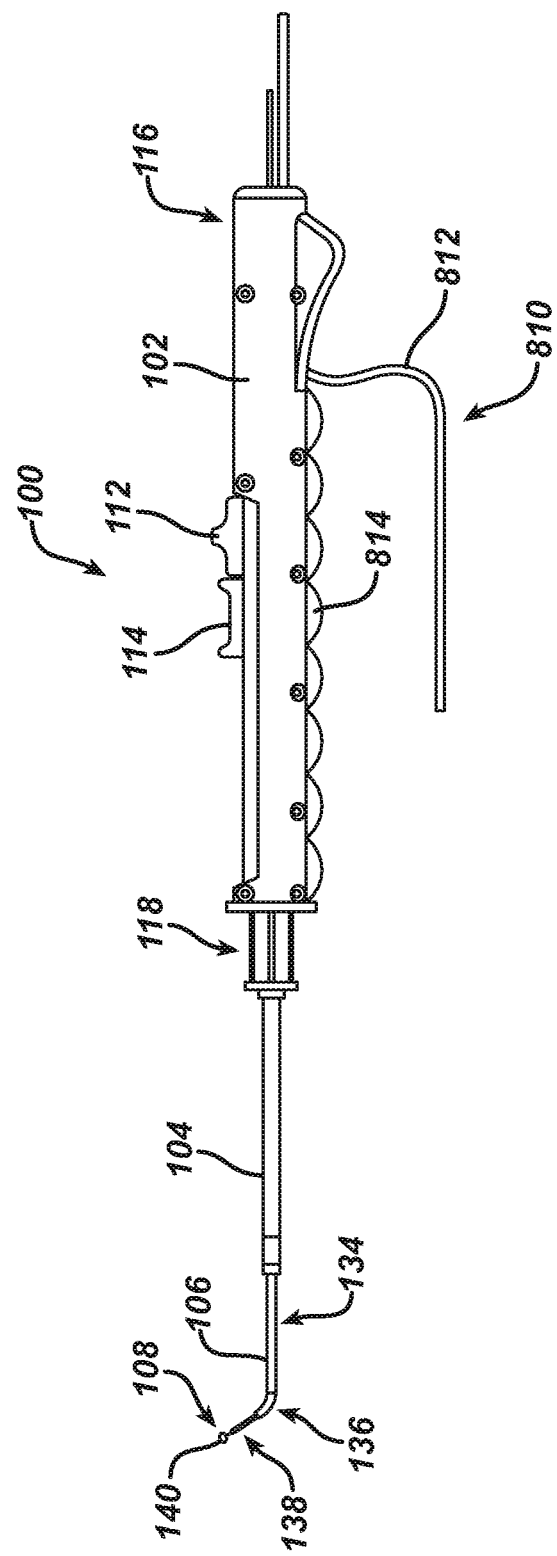
FIG. 19 is an embodiment of the device according to the invention showing a side view of the device with a further handle design.
Figure 20:
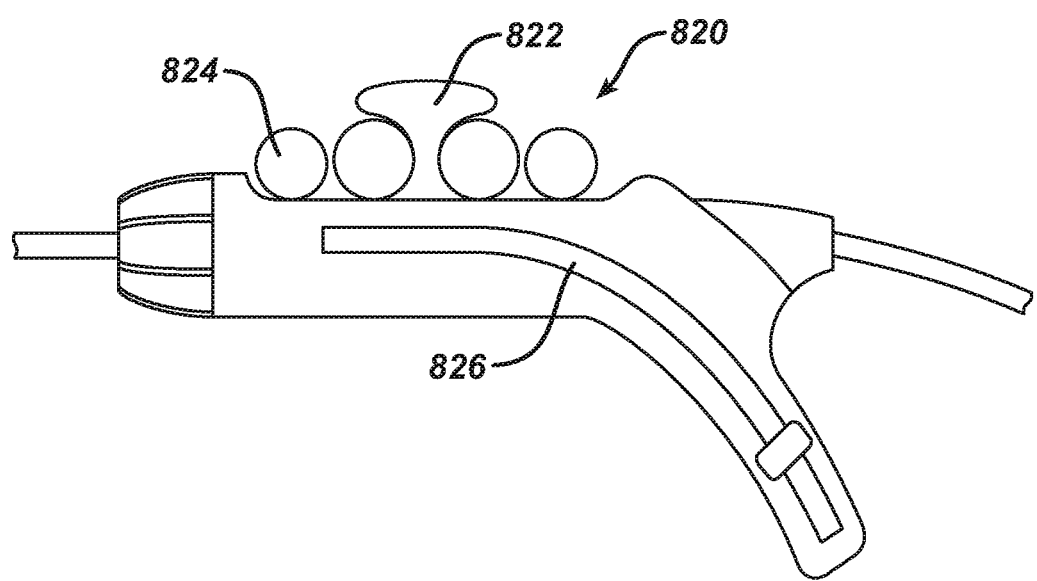
FIG. 20 is an embodiment of the device according to the invention showing a side view of another alternative handle design.

Alternative handle designs for the devices of the invention are shown in FIGS. 18, 19 and 20. In these embodiments, the finger anchoring pegs shown in FIGS. 1 through 5 have been replaced with grips 800, 810 and 820 to keep the device in hand in the absence of active grasping. The grip 800 shown in FIG. 18 comprises a wrap around band 802 designed to fit around the user's hand or fingers and allows the user to relax the hand for periods of time without the fear of the device falling out of the hand. The grip 810 shown in FIG. 19 comprises an open hook 812 designed for engagement of the handle 102 by the user with freedom of motion at the distal end 118 of the handle. The grip 820 shown in FIG. 20 comprises a t-leg 822 and finger-loops 824 designed for engagement of the handle 102. A non-linear actuation track 826 would allow the motion of the movement mechanisms 112 and 114 to be more naturally along the arc of the user's thumb path. In the embodiments shown in FIGS. 18 and 19, rounded projections 804 and 814 are added to the handles to provide easy finger placement.

Grooming sheath 104 has a distal end 124, a proximal end 126 and an atraumatic tip 128 (see FIG. 4 in particular) at distal end 124. Proximal end 126 of grooming sheath 104 is attached to distal end 118 of handle 102 (see FIG. 3 in particular). Grooming sheath 104 can be attached to handle 102 using any suitable technique including, for example, mechanical adaptors known to one skilled in the art.

Grooming sheath 104 is configured to collapse and otherwise groom a balloon catheter 110 during retraction of the balloon catheter into the grooming sheath. Grooming sheath 104 can also, if desired, be configured to provide additional stiffness to rail 106. Grooming sheaths according to embodiments of the present invention are particularly useful in that deflating a balloon catheter via application of vacuum can be sub-optimal in terms of collapsing the balloon catheter into a beneficially small profile. However, retracting a deflated balloon catheter into a grooming sheath may collapse the balloon catheter into a beneficially small profile. Such a small profile provides the beneficial ability to re-advance and re-inflate the balloon in another sinus opening, particularly another sinus opening that the collapsed balloon catheter is accessing through a narrow sinus structure.

Figure 21:
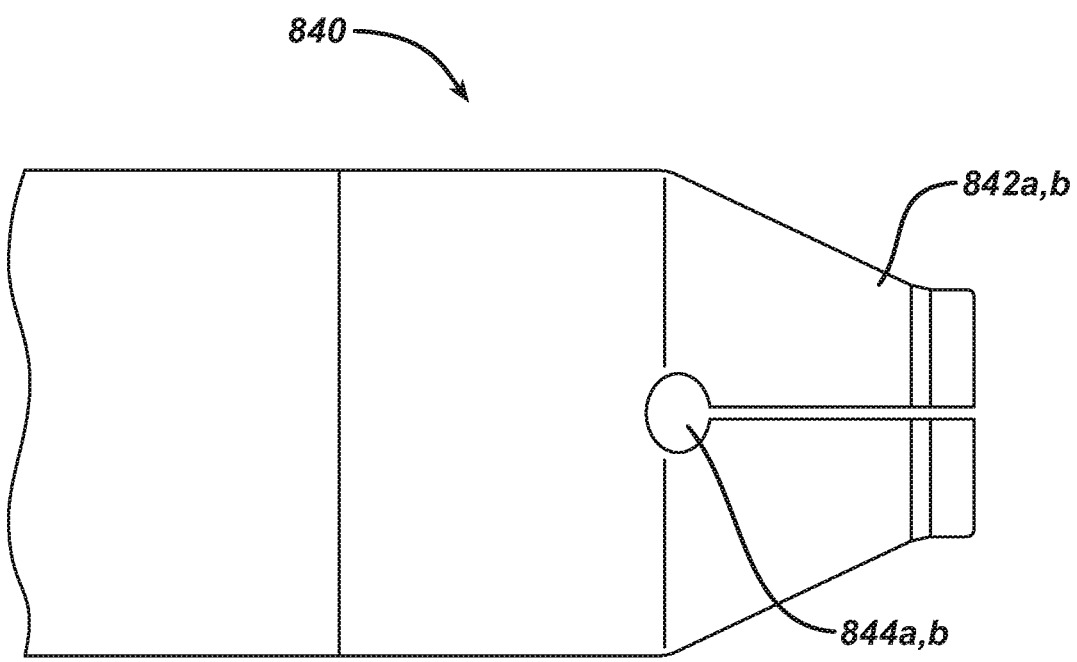
FIG. 21 is a side view of the distal end of a grooming sheath according to the present invention.

Grooming sheath 104 can be constructed of any suitable material or materials including for example, a stainless steel tube with or without a polymer lining (e.g., a Nylon, PTFE or Pebax lining). In the embodiment of FIGS. 1-6, the polymer lining includes an extension 104' that extends slightly from the stainless steel tube at the distal end of the grooming sheath (see FIG. 4 in particular). Atraumatic tip 128 of grooming sheath 104 can be formed, for example, of a low durometer polymer fused with polymer extension 104' or in an alternative embodiment, it may be formed of a low durometer polymer that is thermally fused and attached with a lap joint to the stainless steel tube. The polymer may be colored for endoscopic visualization. The grooming sheath tip 840 may further be tapered down in diameter at the distal region (see FIG. 21) and it may be expandable. This tapered tip 840 provides a transition between the outer diameter of the rail 106 and the inner diameter of the grooming sheath 104, providing a ramp for advancing through tissue to slide past. Two slits 842a and 842b, positioned 180° apart (or alternatively 4 slits positioned 90° apart) are designed for expansion as the balloon passes through the tip 840 and therefore allow for the balloon to exit and re-enter back into the grooming sheath 104 with low friction. The most proximal ends of the slits 842a and 842b (there may be four circular features if there are four slits) have circular features 844a and 844b which are designed to prevent tearing and further proximal propagation of the slits. The sheath 104 of FIG. 18 is shown as ending a distance proximal to the rail curved section 136, but in particular embodiments, it may be extended over close to the rail curved section 136 so that the balloon has less distance to travel when it is advanced out of the sheath.

As shown in FIG. 2, rail 106 has a distal end 130, a proximal end 132 and a rail lumen 133 (see FIG. 12 described below) and is disposed partially within grooming sheath 104 such that an annular lumen 135 is defined between rail 106 and grooming sheath 104. Proximal end 132 of rail 106 is attached to handle 102 (see FIG. 2).

Rail 106 is configured to serve as (i) a probe for finding an access path to the target sinus ostium (also referred to as sinus opening), (ii) to provide a shaped rail to guide the balloon catheter into the sinus ostium, and (iii) to provide a luminal path (i.e., rail lumen 133) for guide wire movement. If desired, the guide wire lumen of the rail can be made with adequate space such that irrigation or suction can be applied via the guide wire lumen during use of the medical device.

Rail 106 can be formed of any suitable material including, for example, 304 stainless steel or 316 stainless steel. In addition, distal end 130 of rail 106 can be manufactured with a predetermined shape that is appropriate for the treatment of a given sinus opening in the range of between about 0 degrees and 125 degrees and the appropriate rail 106 chosen for treatment of a particular sinus. For example, for Frontal sinus access, the predetermined shape can be an angled shape with an angle (bend) in the range of 65 degrees and 85 degrees or of about 75 degrees. For Sphenoid sinus access, the predetermined angled shape can be in the range of about 0 degrees and 30 degrees or approximately horizontal. For maxillary access, the predetermined angled shape can be in the range of about 85 degrees and 125 degrees or of about 100 degrees. For treatment of more than one sinus, the rail 106 can be removed from the handle 102 and replaced with one shaped for a different sinus.

If desired, distal end 130 of rail 106 can be formed of a malleable material that enables a user to configure the shape of distal end 130 prior to inserting medical device 100 into a patient's anatomy. In this circumstance, distal end 130 can be formed of any suitable malleable material known to one skilled in the art. An exemplary but non-limiting malleable material is heat treated (e.g., annealed) stainless steel. A formed feature in a thermoform tray would allow a user to shape the distal end 130 directly in the tray, would aid in the proper shaping of the distal end 130 and prevent the user from using their hands or other instrument with the likely result of damaging the distal end 130.

If desired, distal end 130 of rail 106 can include endoscopic visible markers (not shown in the FIGs.) and/or an atraumatic tip (also not shown in the FIGs.). Such an atraumatic tip can be formed, for example, from a soft polymer material or consist of an appropriately polished and sintered distal end. Such endoscopic visible markers can, for example, be placed on the surface of distal end 130 and be configured to indicate the distance away from the furthermost distal point of the rail. In one embodiment the endoscopic visible markers are configured as thin circumferential bands, with the number of bands corresponding to the number of centimeters the marked location is from the furthermost distal point. For example, if the marked location is 3 cm from the furthermost distal point, the endoscopic visible mark would consist of three thin bands. Such endoscopic visible marks beneficially provide a user with a sense of the location of the tip of the rail and, thus, its extension into a sinus.

In the embodiment of FIGS. 1-6, distal end 130 of rail 106 includes a proximal straight section 134 (such as, for example, a 7 cm straight section), a curved section 136 (e.g., for example, a 3 cm curved section), and a relatively short distal straight section 138 (see FIG. 1) of, for example, 5 mm to 50 mm in length. Typical, but non-limiting, rail inner and outer diameters are 0.038 inches and 0.052 inches, respectively. Such a configuration, along with an extendable guide wire, has been determined to provide for ease of access to sinus openings during treatment thereof.

Figure 22:
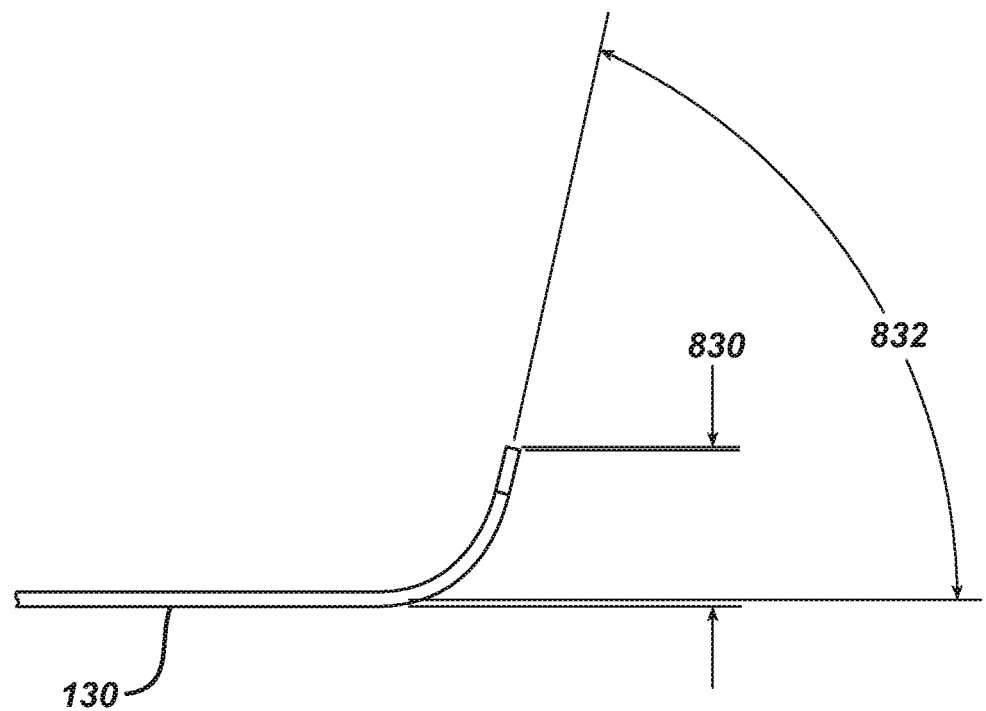
FIG. 22 is a side view of the distal end of the rail of the device according to the present invention.

For optimal sinus access, precise dimensions have been determined for rail 106. In order to ensure an appropriate range of motion during probing of the maxillary sinus, a tip envelope 830 (see FIG. 22) of between about 0.10 inches and 0.50 inches is desirable, or between about 0.20 and 0.40 inches and often about 0.30 inches. Further, to ensure easy access of the maxillary sinus by the guide wire 108 after manipulating the distal end of the device 100 into position, a tip trajectory 832 of between about 85 degrees and 125 degrees is desirable, or between about 90 degrees and 110 degrees and often about 100 degrees. The distal tip may be beveled to provide support to the distal ball, to allow for directionally anterior advancement of the curved guide wire and facilitate retraction of the balloon. To ensure easy access of the frontal sinus by the guide wire 108 after manipulating the distal end of the device 100 into position, a tip envelope 830 of between about 0.40 inches and 0.80 inches is desirable, or between about 0.50 inches and 0.70 inches often about 0.60 inches and a tip trajectory 832 of between about 55 degrees and 85 degrees is desirable, or between about 60 degrees and 80 degrees and often about 70 degrees. The distal tip may be squared or beveled. To ensure easy access of the sphenoid sinus by the guide wire 108 after manipulating the distal end of the device 100 into position, a tip trajectory 832 of between about 0 degrees and 30 degrees is desirable, or between about 0 degrees and 10 degrees and often approximately horizontal.

Figure 23A:
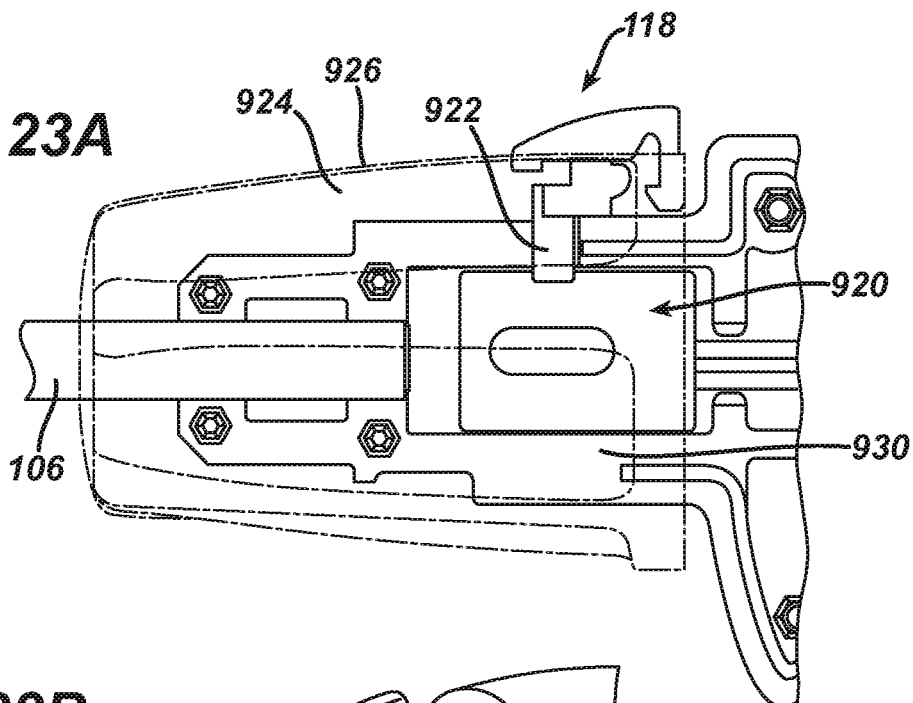
FIGS. 23A and 23B are side and perspective views, respectively
Figure 23B:
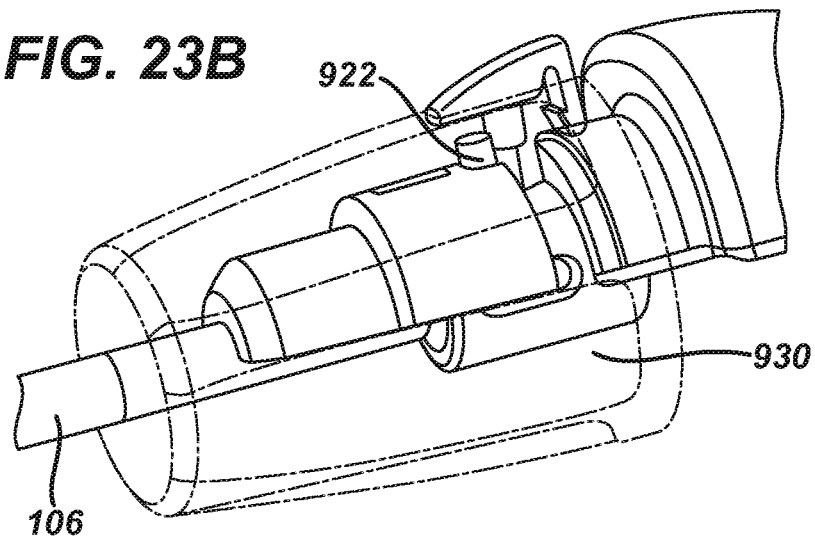
Figure 23C:
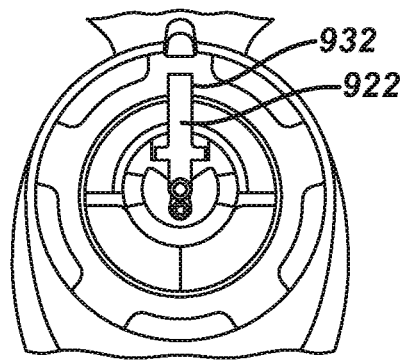
FIGS. 23C and 23D are front views of the distal portion of the device according to the present invention.
Figure 23D:
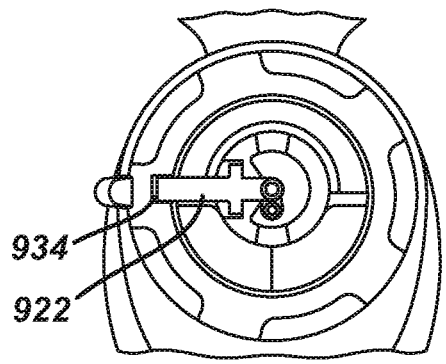

The distal end 130 of rail 106 must further be positioned to allow for the comfort of the user. A right handed user will position the rail differently than a left handed user. Accordingly, the ability to rotate the rail relative to the longitudinal axis of the handle 102 enables the user to orient the rail geometry, the balloon catheter movement mechanism 112 and the guide wire movement mechanism 114 on the handle 102. The mechanism to rotate the rail has five key elements as shown in FIGS. 23A, 23B, 23C and 23D the rail switch 920, the rail switch post 922, the front collar 926, the collar stop 928 and the spring. Referring to FIGS. 23A and 23B, the distal end 118 of the handle 102 is shown. The first element of the mechanism to rotate the rail 106 is the rail switch 920, a molded part that provides a bearing surface for the rail switch post 922. The post 922 extends through the rail switch 920 and through the distal end 118 of the handle 102 and terminates in a channel 924 defined between the front collar 926 and the handle 102. The rail switch post 922 is made of a rigid material, in this case stainless steel, and is welded to the rail 106 through the rail switch 920. The front collar 926 provides a channel 924 for the rail switch post 922. As the front collar 926 is rotated, the rail switch post 922 is moved clockwise or counter clockwise within the keyway 930 as required for appropriate rail orientation. The collar stop 928 locks the rail switch post 922 in a first front collar slot 932. A spring (not shown) provides force against the front collar 926 to hold the rail switch post 922 in a forward position. In order to change positions, the collar 926 is pulled toward the user and twisted so that the rail switch post 922 is pulled out of the first slot 932 in the keyway 930 and can rotate. Once the rail switch post 922 reaches a second slot 934 in the keyway 930 (in the case shown, the second slot 934 is 90 degrees offset from the original slot, but the slots may be 45, 90, 135, or 180 degrees offset or anywhere therebetween, either clockwise of counter clockwise from the first slot 932 and there may be 2, 4, 6, 8 or any number of key slots less than or equal to 12), the spring pulls the post 922 into the second slot 934. Because the rail switch post 922 rotates about a line that is offset from the center of the collar 926, the rail switch post 922 telescopes up and down in the slots 932 and 934.

As shown in FIGS. 1-4, the guide wire 108 operatively extends from the distal end of the rail 106 following the orientation of the rail 106 described above. Guide wire 108 can be either (i) attached to the distal end of the rail and extend beyond the distal end of the rail a predetermined fixed length, or (ii) disposed at least partially in handle 102 and the rail lumen with medical device 100 being configured for advancement and retraction of the guide wire through the handle and rail lumen by longitudinal sliding of guide wire movement mechanism 114 along the handle 102 (compare, for example, FIGS. 2 and 3 which illustrate different guide wire extensions). For the latter configuration, the guide wire can be attached to a guide wire movement mechanism such as element 114 in FIGS. 1-3 and 5.

In the embodiment of FIGS. 1-6, guide wire 108 includes an essentially spherical atraumatic tip 140 (see FIGS. 4 and 6 in particular). Such a spherical atraumatic tip can have, for example, a diameter in the range of approximately the same diameter as the guide wire (e.g., 0.032 inches) to 0.080 inches. The upper limit of the spherical atraumatic tip diameter is chosen such that the tip does not unduly prevent the guide wire from tracking in a tight sinus access path. In one embodiment, the rail has a diameter of approximately 0.050 inches and the spherical atraumatic tip of the guide wire has a diameter of 0.060 inches such that the spherical tip shields the furthermost distal edge of the rail from contact with sinus or other tissue of the patient's anatomy during use of the medical device. Alternatively, the spherical tip of the guide wire can be sized such that the balloon catheter can extend beyond the spherical tip.

The tip of guide wire 108 can, if desired, be lighted in a manner that enables a user to confirm successful access to a sinus opening. Such tip may be formed as a molded component that will be adhesively bonded to the guide wire 108, but it must be translucent to allow full light output to transmit through the tip.

Guide wire 108 can be formed of any suitable material known to one skilled in the art including, for example, stainless steel, Nitinol and combinations thereof and of any suitable stiffness or graded stiffness. In addition, guide wire 108 can be configured in any suitable manner including, for example, a stainless steel wound coil, a coil wound around a central core wire (including a core wire of varying diameter that provides a varying stiffness down the length of the guide wire), a configuration with an angled distal end (e.g., a 5-30 degree angle end with a length of 2.0 to 10 mm), and configurations that include the incorporation of one or more light transmitting fibers that provide for a lighted guide wire distal end and/or tip formed of light transmitting material and one or more stiffening materials (such as a hypotube) that prevent buckling of the guide wire in the device of in the patient's anatomy. Other configurations may include a sensor on the tip for tracking (for example, a coil that is energized that creates a magnetic field), or a lens on the tip for greater dispersion of light from the tip. Suitable lighted guide wires that may be incorporated in the current device are described, for example, in US 2008/0228085, issued as U.S. Pat. No. 9,820,688 on Nov. 21, 2017, which is herein incorporated by reference in its entirety.

Figure 24:
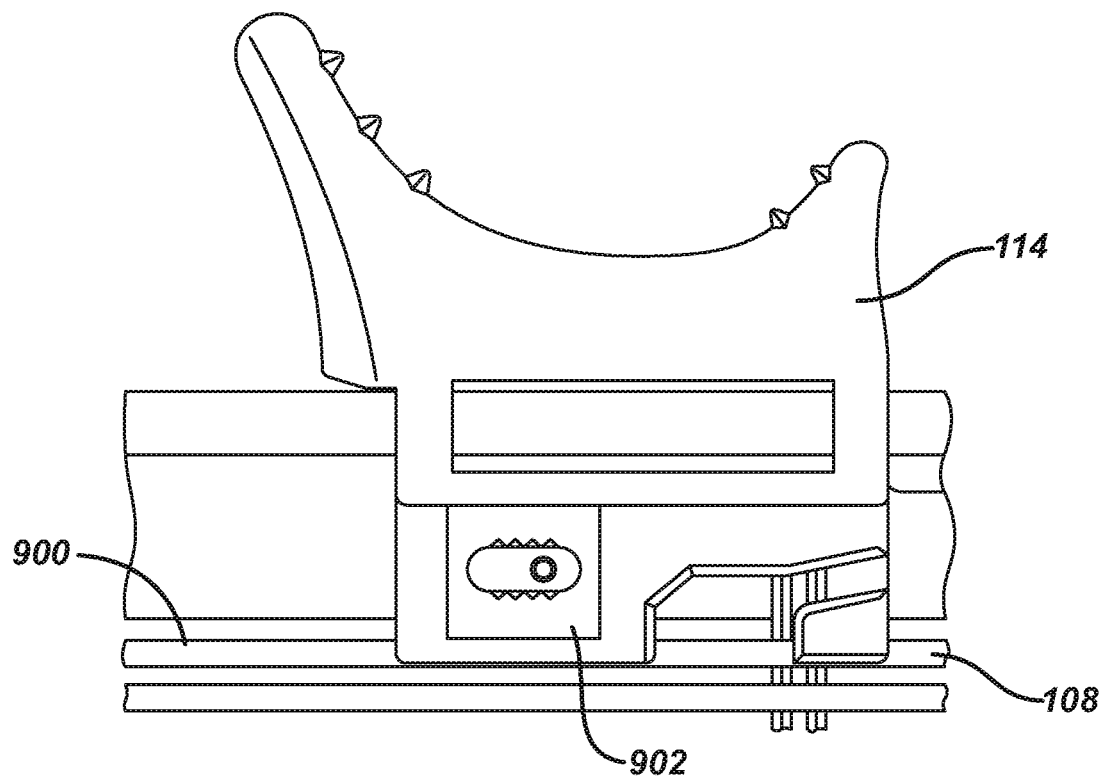
FIG. 24 is an enlarged side view of the guide wire movement mechanism according to the present invention.

For additional tactile feedback for the user for accessing the sinus, a number of additional features may be incorporated into the handle 102 as will be further described with regard to FIG. 24. In this embodiment, in order to prevent buckling of the guide wire 108 between the rail 106 and the distal portion of the guide wire movement mechanism 114, a hypotube 900 may be soldered or welded to the guide wire 108 and a fin 902 soldered or welded to the hypotube to connect the guide wire movement mechanism 114 to the hypotube 900. Alternatively, rather than a fin 902, a tube or bushing may be placed around the hypotube, a post with a through hole for the hypotube, a split leg fin welded on either side of the hypotube, or a glue connection directly to the guide wire movement mechanism may be useful to connect the guide wire movement mechanism to the hypotube. In this way, the force that is applied to the guide wire movement mechanism to advance it along the handle 102 directly translates into movement of the guide wire 108 into the sinus anatomy. When an obstacle is encountered, the guide wire movement mechanism 114 will no longer advance and the user will know that there is an obstacle. Alternatively, rather than a hypotube, it may be desirable to increase the diameter of the internal core wire of the guide wire 108 or to add a stiffening member to provide stiffness to the guide wire 108 between the rail 106 and the guide wire movement mechanism 114. In addition, when the rail 106 is rotated for advancement into the right or left maxillary sinus or for appropriate orientation for a right or left handed user, the tube or bushing placed around hypotube 900 will allow for rotation of the guidewire 108 with the rail 106 so that it too will be appropriately positioned for the sinus and/or the handedness of the user.

Guide wire 108 serves to provide additional reach, beyond the reach of the rail, into target anatomy in a safe manner. For a guide wire of predetermined fixed length, the length can be, for example, in the range of 5 mm to 30 mm. For a medical device configured with an extendable guide wire, the configuration can be such that a user can extend the guide wire from the rail for a distance of, for example, 1 mm to 50 mm.

Balloon catheter 110 is disposed at least partially in handle 102 and the annular lumen between the rail 106 and the grooming sheath 104 (see, for example, FIG. 12 described below). Moreover, balloon catheter 110 is operatively connected with balloon catheter movement mechanism 112. In this regard, balloon catheter movement mechanism 112 is configured for advancement and retraction of the balloon catheter 110 through the handle 102 and annular lumen 135 and along the rail 106 and guide wire 108 by longitudinal sliding of the balloon catheter movement mechanism 112 along the handle 102. However, once apprised of the present disclosure, one skilled in the art will recognize that balloon catheter movement mechanisms employed in medical devices (and methods) according to the present invention are not limited to those that are user operated via longitudinal sliding along the length of the handle. Rather, user operation of the balloon catheter movement mechanism can be any suitable operation that results in operable movement of the balloon catheter by, for example, translation of the balloon catheter movement mechanism relative to the handle or rotation of a balloon catheter movement mechanism component. In this regard, the configuration of the balloon catheter mechanism would support such user operation via suitable rack and pinion mechanism, gear-based mechanisms, threaded mechanism and/or electromechanical means.

A suitable rack and pinion mechanism can be incorporated into devices according to embodiments of the present invention by, for example, employing a configuration wherein a balloon catheter shaft disposed within the handle is attached to a rack gear. Such a rack gear can be configured for longitudinal movement by engagement with a roller gear that is operated (i.e., rotated) by a user. Between the roller gear and the rack gear, there can be a gear train that includes various combinations of gear ratios providing a reduction in the force required to be exerted by a user at the roller and/or increasing travel distance for the rack with a small rotation actuated at the roller.

A suitable threaded mechanism can be incorporated, for example, by attaching the balloon catheter to a cylindrical component with external threads with the cylindrical component being constrained to move longitudinally without rotation. A roller with internal threads can be configured to engage with the external threads of the cylindrical component. In such a configuration, user operation via rotation of the roller causes the cylindrical component and the balloon catheter to move longitudinally. The thread design of such an embodiment can be configured with threads of a predetermined pitch or type (e.g., 3 start thread) to provide greater travel distance by the catheter for a lesser rotation of the roller.

Figure 9:
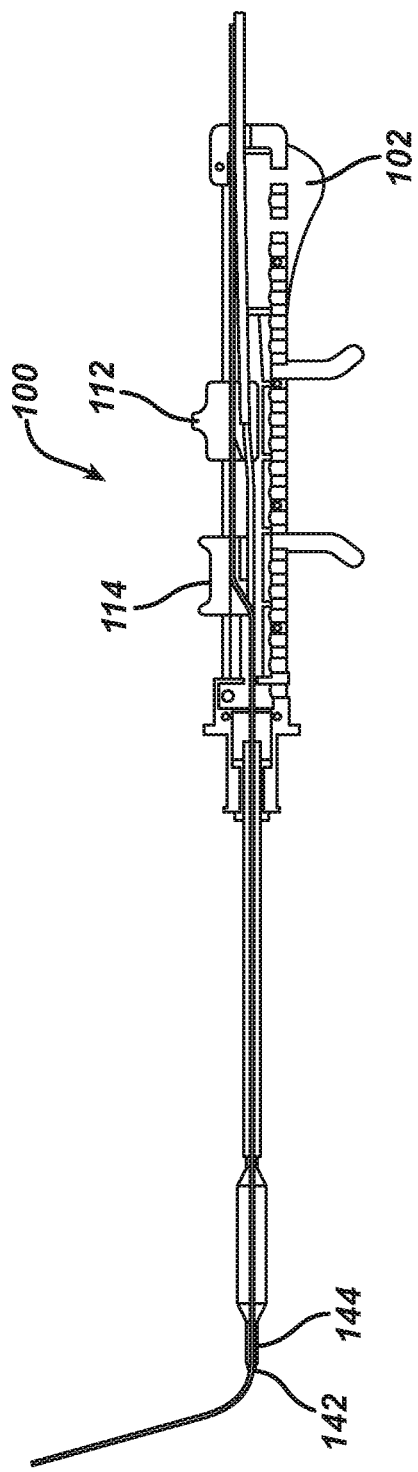
FIG. 9 is a simplified side cross-sectional depiction of the medical device of FIG. 8.

Balloon catheter 110 can be any suitable balloon catheter known to one skilled in the art including, for example, dual shaft balloon catheters with a braided inner shaft formed of Nylon, PET and Pebax. A braided inner shaft provides for stiffness so that the balloon remains in line with the curve of the rail when advanced distal to the rail and inflated. As shown in FIG. 9, a soft tapered balloon tip 142 on the distal extension 144 to the braided inner shaft provides for a smooth profile transition to the smaller guide wire 108 and allows for advancement of the balloon around the curve of the rail and placement into the target anatomy. The balloon catheter can also, if desired, include a lubricity layer to reduce friction between the rail and the catheter balloon. The balloon catheter may be any size catheter including but not limited to 3.5 mm to 7 mm in diameter (when inflated) and 12 mm to 24 mm in working length (for example 3.5 mm×12 mm, 5 mm×16 mm, 5 mm×24 mm, 6 mm×16 mm, 6 mm×20 mm, 6 mm×24 mm, 7 mm×16 mm and 7 mm×24 mm. In one embodiment for the maxillary sinus, the dimensions of the working portion of the balloon catheter are 6 mm in diameter (when inflated) and 24 mm in working length. The balloon catheter 110 further may have a conformable distal tip such that it is flush with the outer diameter of the guidewire 108 when it is expanded distally over the distal end of rail 106. Materials useful for such purpose include but are not limited to stainless steel, nitinol, a coil, or laser cut tubing, of a tip conformation similar to that of the grooming sheath described above, with two slits spaced 180 degrees apart (or four slits 90 degrees apart).

Prior to use of the medical device, the balloon catheter 110 is retracted within the grooming sheath 104 and handle 102. When extended, part or the entirety of the balloon working length of the balloon catheter extends distal to the tip rail over the guide wire. In one embodiment, the balloon catheter does not extend beyond the tip of the guide wire. If the tip of the guide wire is of a sufficient diameter and the guide wire is not fully extended when the balloon catheter is extended, extension of the balloon catheter can carry the guide wire with it. In another embodiment, the guide wire tip is smaller than a lumen of the balloon catheter. In this embodiment, the balloon catheter can extend beyond the tip of the guide wire.

Guide wire movement mechanism 114 is configured for advancement and retraction of the guide wire through the handle 102 and rail lumen 133 by longitudinal sliding of the guide wire movement mechanism 114 along the handle 102.

However, once apprised of the present disclosure, one skilled in the art will recognize that guide wire movement mechanisms employed in medical devices (and methods) according to the present invention are not limited to those that are user operated via sliding along the length of the handle. Rather, user operation of the guide wire movement mechanism can be any suitable operation that results in operable movement of the guide wire by, for example, translation (i.e., movement that changes the position of an object) of the guide wire movement mechanism relative to the handle or rotation of a guide wire movement mechanism component. In this regard, the configuration of the guide wire movement mechanism would support such user operation via, for example, a suitable rack and pinion mechanism, gears, and/or electromechanical means.

Figure 25:
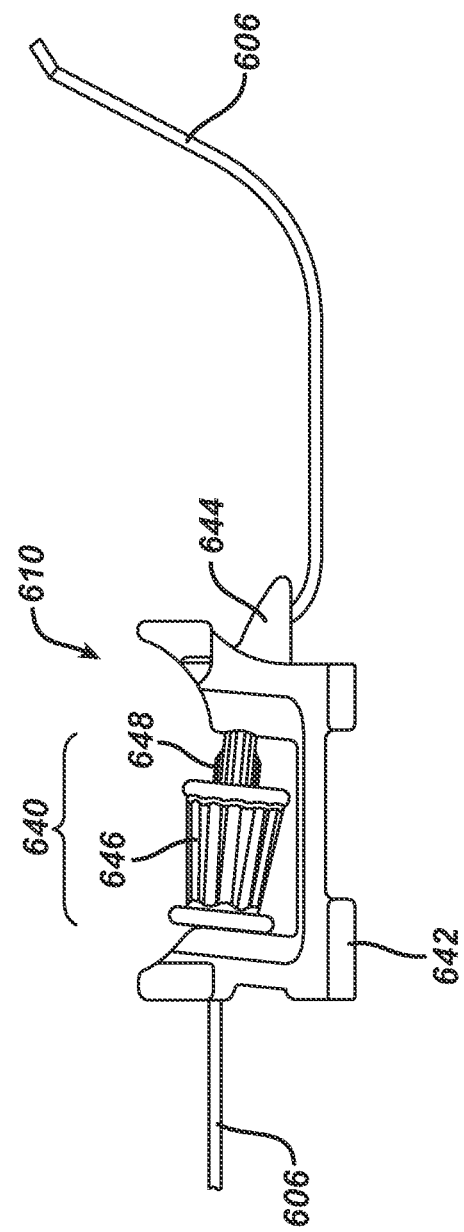
FIG. 25 is a simplified side view of an alternative guide wire movement mechanism and guide wire of the medical device according to the invention.
Figure 26:
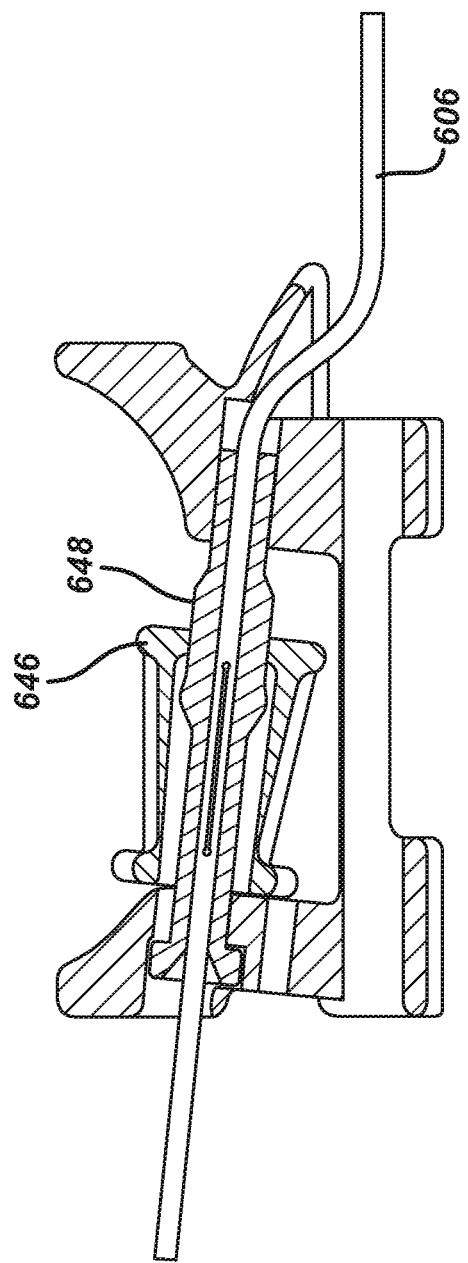
FIG. 26 is a simplified cross-sectional view of the guide wire movement mechanism and guide wire of FIG. 25 in a locked position.

In an alternative embodiment shown in FIG. 25, guide wire movement mechanism 610 may include an integrated guide wire locking and rotation mechanism 640 configured for rotation of guide wire 606 and for securely locking and unlocking the guide wire to the guide wire movement mechanism 610, a rail 642, and a nosepiece 644. Rail 642 is configured for slidably attaching guide wire movement mechanism 610 to handle 102. Nosepiece 644 is configured to direct guide wire 606 into handle 102 and rail lumen 133 of rail 106 as described above.

Integrated guide wire locking and rotation mechanism 640 includes a barrel 646 and a collet axle 648 (see FIGS. 25-29 in particular). The locking/unlocking capability of integrated guide wire locking and rotation mechanism 640 enables a user to adjust the length of the guide wire extending (distally) beyond the guide wire movement mechanism 610.

Figure 27:
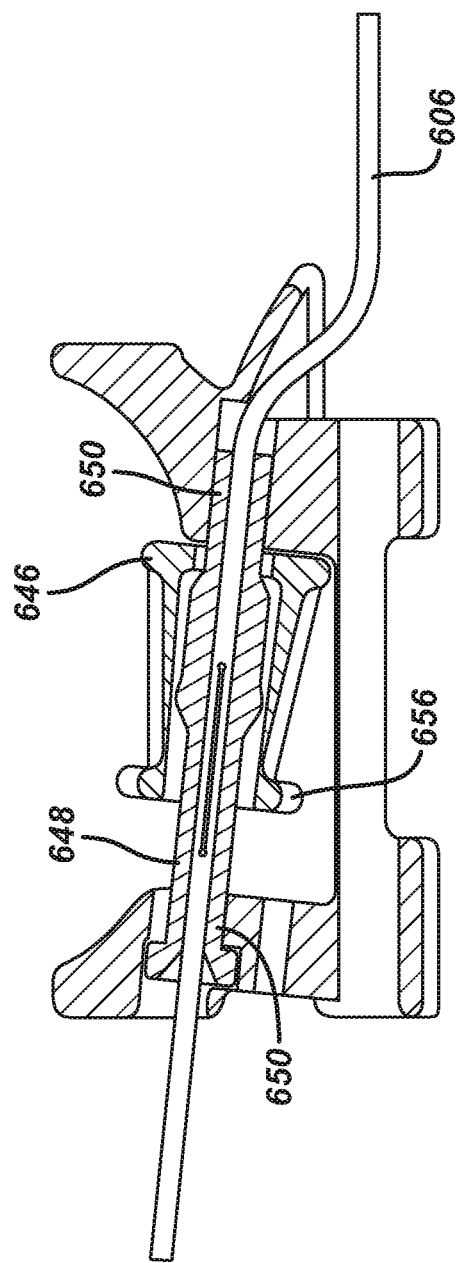
FIG. 27 is a simplified cross-sectional view of the guide wire movement mechanism and guide wire of FIG. 25 in an unlocked position.
Figure 28:
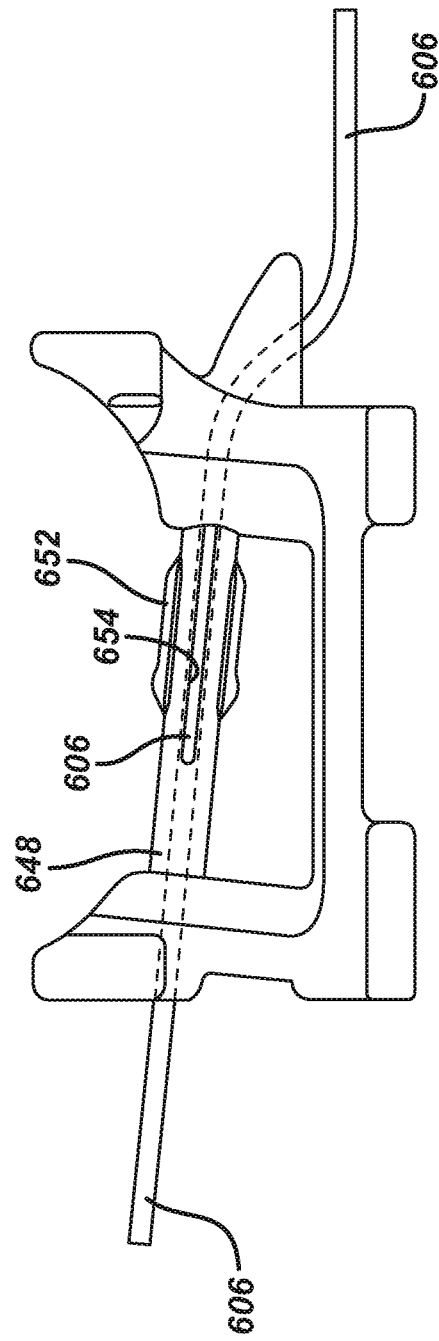
FIG. 28 is a simplified transparent view of the guide wire movement mechanism and guide wire of FIG. 25 in the absence of the barrel of the guide wire movement mechanism.

Collet axle 648 is configured to function both as a collet and as an axle and has a longitudinal opening through which the guide wire 606 passes (see FIG. 27 in particular). In the embodiment of FIGS. 25 through 29, collet axle 648 is essentially cylindrical in overall shape, and when locked onto the guide wire (see FIG. 26 where the depicted overlap of the barrel and the collet axle serves to illustrate that the barrel is compressing the collet axle onto the guide wire), rotates with the guide wire 606. Collet axle 648 rotates within bearing surfaces 650 of the guide wire movement mechanism 610 (see FIG. 27). The collet axle has a plurality of alternating protrusions 652 and slots 654 (see FIG. 27) configured to lock (close) onto the guide wire, thereby linking rotation of the guide wire with rotation of the collet axle. Collet axle 648 exerts a strong clamping force on the guide wire when the collet axle is tightened via longitudinal movement of barrel 646 (as is evident from a comparison of FIG. 25 where the collet axle is locked into the guide wire and FIG. 26 where the collet axle is unlocked from the guide wire).

Barrel 646 has an essentially cylindrical cross-section and an opening therethrough, in which collet axle 648 is disposed. The contour of the barrel's opening is designed to receive the collet axle and has at least one focal point configured to collapse the collet axle onto the guide wire (see FIG. 25 in particular). The exterior of barrel 646 has grip features shown in the embodiment of FIGS. 25-26 as a macroscopic surface feature (i.e., ridges). However, such grip features could alternatively be microscopic in nature or based on frictional material properties such as a rubberized surface. Such grip features provide traction for the user to rotate or translate the barrel via operation with, for example, the user's thumb. The distal and proximal ends of the barrel have a raised ring feature 656, which provides traction for the user to translate the guide wire movement mechanism when the collet axle is in a locked position or provide a gripping feature to move the barrel 646 relative to the remainder of the guide wire movement mechanism 610 to lock and unlock the axle 648.

Figure 29:
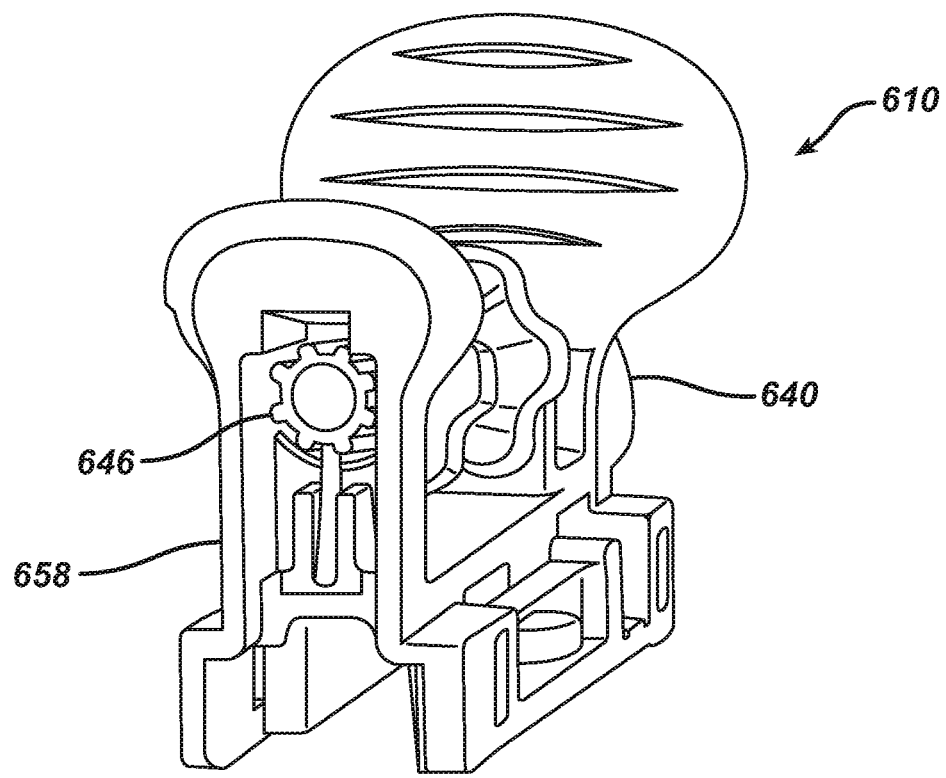
FIG. 29 is an enlarged perspective view of the guide wire movement mechanism of FIG. 24.

The guide wire movement mechanism 610 is shown in detail in FIG. 29 and allows for advancing, retracting and rotating the guide wire 606. The mechanism 610 integrates a guide wire locking and rotation mechanism 640 configured for rotation of the guide wire 606 and for securely locking and unlocking the guide wire 606 to the guide wire movement mechanism 610 as further described with regard to guide wire locking and rotation mechanism 640 above. Included in FIG. 29 is clicker 658 that interacts with the fins of barrel 646 to provide audible and tactile feedback of rotation of the locking and rotation mechanism 640 and the resultant rotation of the guide wire 606. A representative guide wire 606 incorporated in the device 100 of the invention is the Relieve Luma Sentry™ Sinus Illumination System manufactured by Acclarent, Inc., Menlo Park, Calif., a guide wire system that can be connected to a light source for transillumination, illumination and subsequent transcutaneous visualization of the sinus cavity.

Once apprised of the present disclosure, one skilled in the art will recognize that guide wire locking and rotation mechanisms employed in medical devices according to the present invention can take any suitable form in addition to the barrel and collet axle configurations shown in, for example, FIGS. 25 through 29. For example, the barrel could be shaped essentially as a sphere, cylinder or other suitable shape.

In general, methods for treating a sinus opening according to embodiments of the present invention include inserting a medical device for the treatment of a sinus opening partially into a patient's anatomy (e.g., a patient's nostril) and subsequently positioning a guide wire operatively extending from a rail of a medical device into a sinus opening of the patient. The methods also include advancing a balloon catheter from an annular lumen of the medical device and along both the rail of the medical device and the guide wire. In the methods, the annular lumen is between the rail and a grooming sheath of the medical device and the advancing is accomplished via sliding movement of a balloon catheter movement mechanism of the medical device along a handle of the medical device. The method also includes treating the sinus opening via inflation of the balloon catheter.

Methods according to embodiments of the present invention are beneficial in that they are, for example, particularly efficient with respect to positioning the balloon catheter for treatment of the sinus opening and retracting the balloon catheter into the medical device. Moreover, the methods provide for the entire method to be conveniently and efficiently conducted using a single medical device and may be performed in hospital operating room setting or in a medical office.

Figure 7:
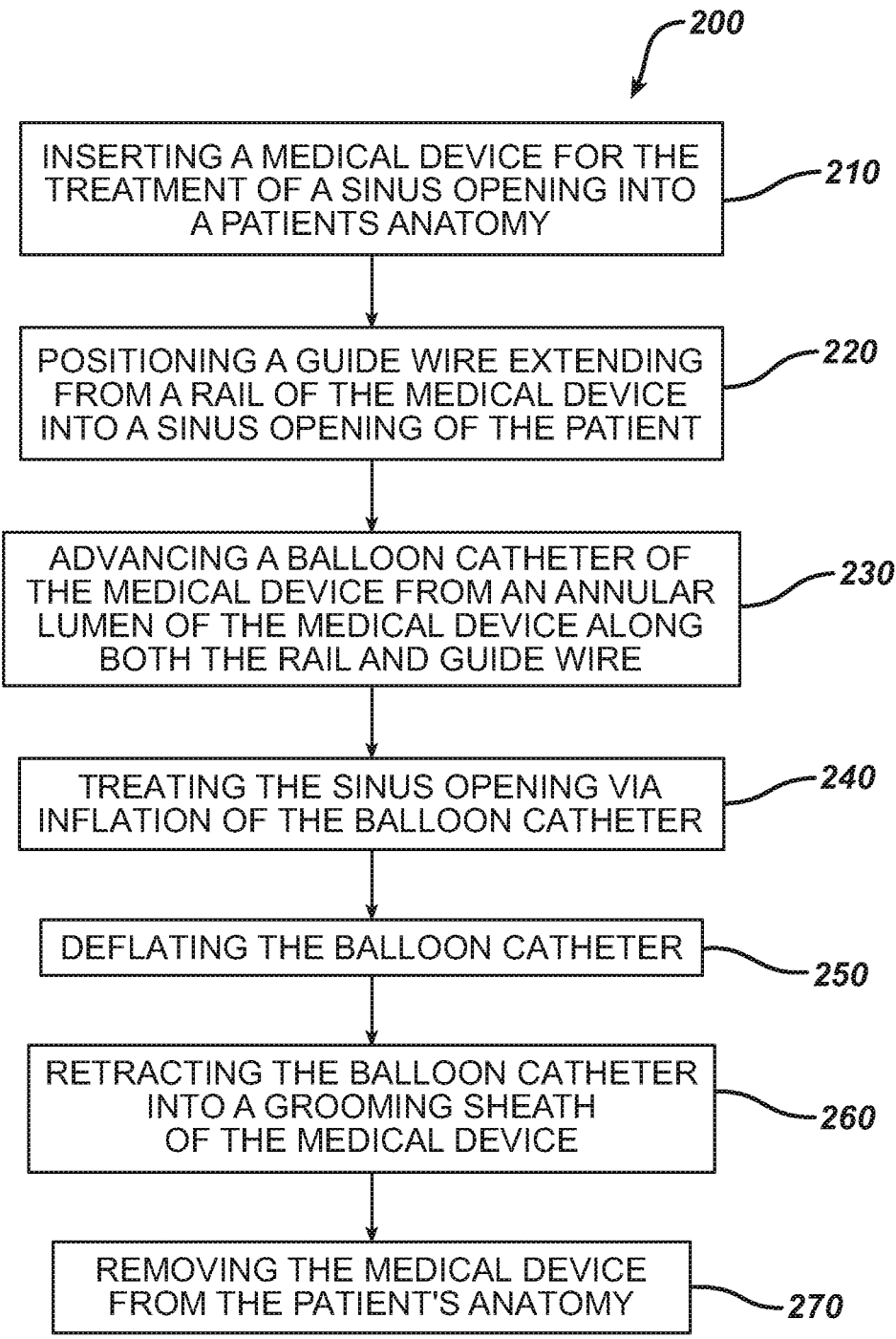
FIG. 7 is a flow diagram depicting stages in a method for treating a sinus opening according to an embodiment of the present invention.

Referring to FIG. 7, method 200 for treating a sinus opening according to an embodiment of the present invention includes inserting a medical device for the treatment of a sinus opening partially into a patient's anatomy (see step 210 of FIG. 7).

At step 220, a guide wire operatively extending from a rail of a medical device is positioned into a sinus opening of the patient.

Subsequently and as noted in step 230 of FIG. 7, a balloon catheter of the medical device is advanced from an annular lumen of the medical device along both the rail of the medical device and the guide wire. Alternatively, the balloon catheter can be advanced solely over the rail and, in a future step, inflated solely over the rail as described below. It is noted that the annular lumen referenced in step 230 is between the rail and a grooming sheath of the medical device. Moreover, in step 230 the advancing is accomplished via sliding movement of a balloon catheter movement mechanism of the medical device along a handle of the medical device.

Method 200 also includes, at step 240, treating the sinus opening via inflation of the balloon catheter. The balloon working segment of the (also referred to as a working portion) balloon catheter can be inflated, as appropriate depending on the positioning of the rail and guide wire, solely over the rail, partially over the rail and partially over the guide wire, solely over the guide wire, or extending beyond the guide wire. Following treatment, the balloon catheter is deflated (step 250), and retracted into the grooming sheath of the medical device (see step 260). At step 270, the medical device is removed from the patient's anatomy.

Once apprised of the present disclosure, one skilled in the art will recognize that method 200 can be readily modified to incorporate any of the techniques, benefits and characteristics of medical devices according to embodiments of the present invention and described herein. For example, methods according to embodiments of the present invention can also include, as part of the positioning step, advancing the guide wire from a rail lumen of the rail via a sliding movement of a guide wire movement mechanism of the medical device along a handle of the medical device. Such a method could also include, following the treating step, retracting the balloon catheter into the grooming sheath and retracting the guide wire into the rail lumen. Moreover, one skilled in the art will also recognize that methods according to embodiments of the present invention, including method 200, can be modified to incorporate suitable sinus opening treatment techniques and steps known to one skilled in the art including suitable techniques and steps described in U.S. Pat. Nos. 7,462,175, 7,500,971, and 7,645,272, and U.S. Patent Application Publications 2008/0281156, issued as U.S. Pat. No. 9,167,796 on Oct. 27, 2015, and 2010/0030113, issued as U.S. Pat. No. 8,979,888 on Mar. 17, 2015, each of which is hereby incorporated in full by reference.

Figure 8:
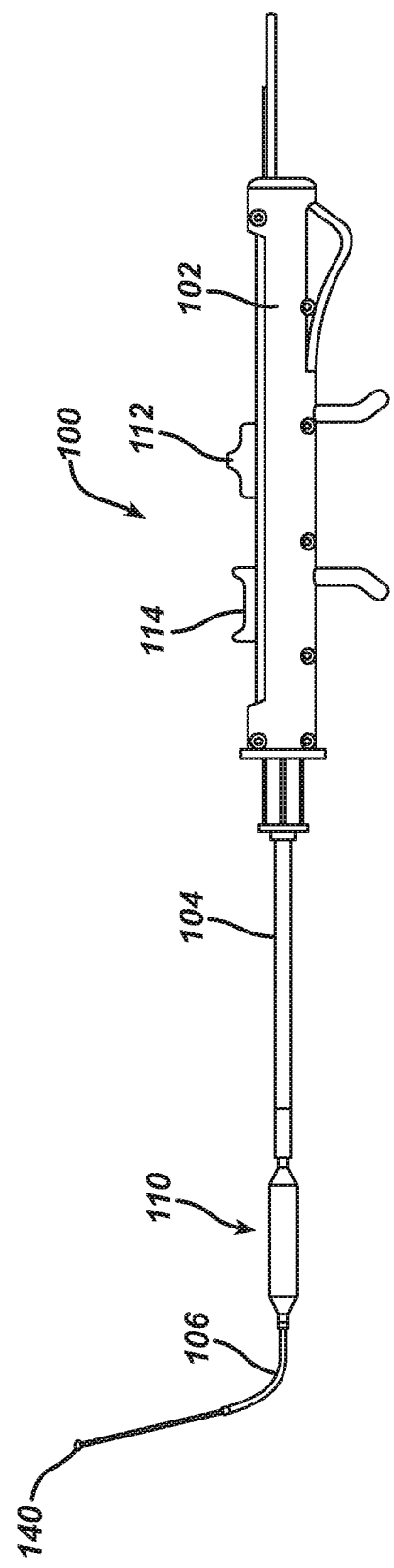
FIG. 8 is a simplified side view depiction of the medical device of FIG. 1 with the guide wire and balloon catheter of the medical device extended and the balloon catheter inflated over the rail.

Referring again to medical device 100, FIG. 8 is a simplified side view depiction of the medical device 100 with the guide wire and balloon catheter of the medical device extended and the balloon catheter inflated over the rail. FIG. 9 is a simplified side cross-sectional depiction of the medical device 100. FIG. 10 is a simplified side cross-sectional depiction of a portion of medical device 100. FIG. 11 is another simplified side cross-sectional depiction of a portion of medical device 100 and FIG. 12 is a combination of a side view and multiple cross-sectional views taken along various lines of the side view of medical device 100.

Referring to FIGS. 8 through 12, handle 102, grooming sheath 104, rail 106, guide wire 108, balloon catheter 110, balloon catheter movement mechanism 112 and guide wire movement mechanism 114, and rail lumen 133 are depicted. Balloon catheter 110 of medical device 100 includes an inner shaft 150 and an outer shaft 152 (see FIG. 12). FIG. 11 depicts how grooming sheath 104 is attached to the inner diameter (ID) of a bushing 190 of handle 102 and how rail 106 is attached to handle 102 by a fin 192. Rail 106 can be, for example, soldered or welded to fin 192 and fin 192 mechanically fastened or adhesive bonded to the remainder of handle 102.

FIG. 13 is a simplified depiction of a balloon catheter sub-assembly 300 as can be employed in embodiments of the present invention. FIGS. 14A and 14B are simplified side and cross-sectional views of balloon catheter sub-assembly 300.

Referring to FIGS. 13, 14A and 14B, balloon catheter sub-assembly 300 includes a balloon catheter 302, a balloon catheter movement mechanism 304 and an inflation tube 306. Balloon catheter 302 includes a balloon working segment 310, distal shaft portion 312, mid-catheter joint 314, a flat lumen shaft 316, inner shaft 318, and outer shaft 320.

Inner shaft 318 and outer shaft 320 are configured such that a rail lumen 322 and an annular inflation lumen 326 are formed in distal shaft portion 312 (see cross-section 360 of FIG. 14B taken along line B-B of FIG. 14A). At mid-catheter joint 314, rail lumen 322 and inflation lumen 328 are in a stacked configuration (see cross-section 370 of FIG. 14B taken along line C-C of FIG. 14A). Cross-section 380 of FIG. 14B (taken along line D-D of FIG. 14A) and cross-section 370 both depict a configuration wherein the flat lumen shaft 316 defines the inflation lumen. Cross-section 350 of FIG. 14B (taken along line A-A of FIG. 14A) depicts the configuration of inner shaft 318 and balloon working segment 310.

Balloon working segment 310 can be made of any suitable material including, for example, polymeric materials such as Pebax, Nylon and PET. The diameter of the balloon working segment can be, for example, in the range of 3.00 mm to 8.00 mm (inflated) and have a length in the range of, for example, 5 mm to 30 mm, with a typical length being in the range of 20 mm to 25 mm. The balloon catheter inner and outer shafts can be made of any suitable material including, for example, polymers such as Pebax, Nylon, Hytrel or high density polyethylene (HDPE). In some embodiments, the inner shaft may be of braided construction to increased stiffness such that the balloon remains coaxial with the rail when advanced distal to the rail and inflated. To reduce friction between the balloon catheter and a rail, the inner shaft can be formed, for example, of a polymer impregnated with micro-particles of PTFE (Polytetrafluoroethylene) or have a PTFE thin liner fused on the inside of the lumen. The balloon may be attached to the inner and outer shafts by thermal or laser bonding.

Inflation lumen shaft 316 can be formed, for example, of metallic tubular material such as a stainless steel tubular material. Inflation lumen shaft 316 can be manufactured, for example, by flattening a round tube of stainless steel. Inflation lumen shaft 316 serves to (i) provide a lumen for inflation and deflation of the balloon working segment and (ii) provide a suitable stiffness to advance and retract the balloon catheter while resisting buckling. In one embodiment, cross-section of inflation lumen shaft 316 is flat and can have any suitable ratio of flat height to flat width (depicted in cross-section 380) with a particularly beneficial ratio being a ratio of 1:1.

Figure 15:
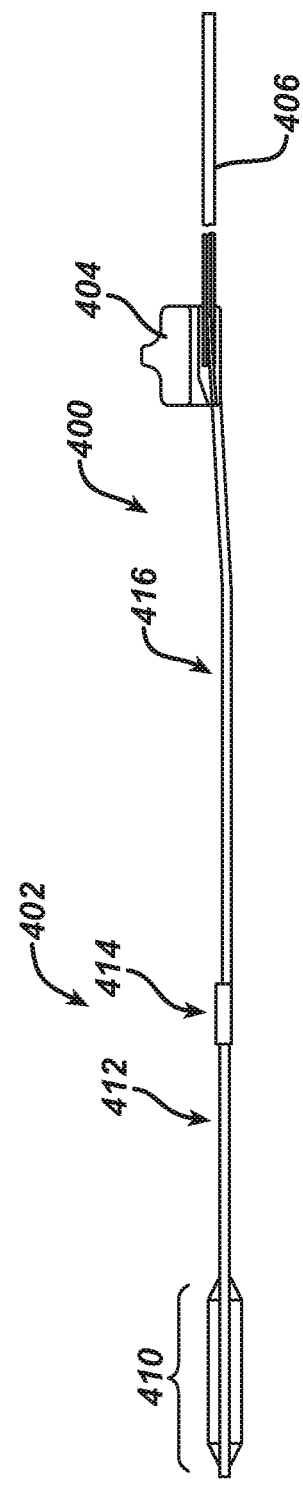
FIG. 15 is a simplified depiction of another balloon catheter sub-assembly as can be employed in embodiments of the present invention.

FIG. 15 is a simplified depiction of another balloon catheter sub-assembly 400 as can be employed in embodiments of the present invention. FIG. 16 is a simplified cross-sectional view of a portion of the balloon catheter sub-assembly of FIG. 15.

Referring to FIGS. 15 and 16, balloon catheter sub-assembly 400 includes a balloon catheter 402, a balloon catheter movement mechanism 404 and an inflation tube 406. Balloon catheter 402 includes a balloon working segment 410, distal shaft portion 412, mid-catheter joint 414 and a flat lumen shaft 416. Flat lumen shaft 416 is assembled into balloon catheter movement mechanism 404 at a slight downward angle (see FIG. 16). Such a downward angle serves to prevent buckling since the downward angle biases any buckling toward the downward direction (which is a direction that can be reinforced by support from the handle as depicted in the handle of FIG. 11).

FIG. 16 depicts the joint between flat lumen shaft 416 and inflation tube 406 inside of balloon catheter movement mechanism 404. FIG. 16 also depicts a clearance hole 420 for a guide wire, the angular entry of the flat lumen shaft 416 (which forces the flat lumen shaft to bend downward under any buckling forces) and the overlapping joint between the flat lumen shaft 416 and the inflation tube 406.

During manufacturing, the flat lumen shaft and inflation tube are first joined together by techniques such as adhesive or heat bonding. In such heat bonding, a polymeric shrink tube is placed over the overlapping joint segment. The assembly is then placed inside of a heat source (e.g., a hot air, RF energy, or laser energy heat source) to melt the polymeric shrink tube and fuse it securely around a metallic flat lumen shaft. The joined segment is then placed inside the balloon catheter movement mechanism as shown in FIG. 16. Adhesive is then used to bond the joined flat lumen shaft and inflation tube inside of the balloon catheter movement mechanism.

Figure 17B:
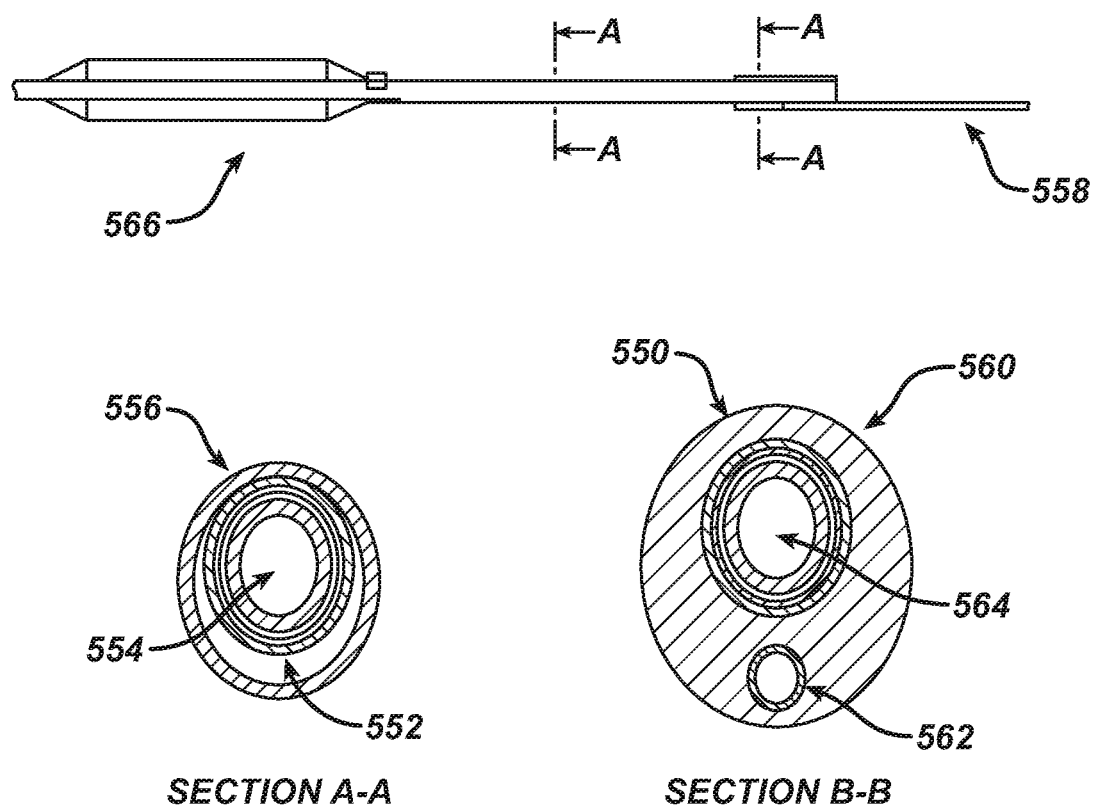

FIG. 17A is a simplified cross-sectional view of a balloon catheter 500 as can be employed in embodiments of the present invention. FIG. 17A shows an exemplary, but non-limiting balloon catheter 500. A balloon distal inner shaft 502, distal outer shaft 504 and proximal shaft 516 are heat fused together at a mid-catheter joint 506. The inner shaft 502 comprises a guide wire lumen 508 and the outer shaft 504 comprises a distal annular lumen 505 which also serves as the inflation lumen. The mid-catheter joint 506 is formed such that the guide wire can exit from the catheter and the inflation lumen transitions from a distal annular lumen 505 (see cross-section 510 taken along line A-A of FIG. 17A) to a single lumen 507 (see cross-section 512 taken along line C-C of FIG. 17A). As shown in cross-section 514 taken along B-B in FIG. 17A, in order to allow for the free movement of the balloon catheter mechanism 112 and the guide wire movement mechanism 114 shown in FIGS. 1-5, the inflation tube (not shown) and attached proximal balloon shaft 516 must be off center with regard to the balloon 518 such that the guide wire lumen 508 and inflation lumen 509 are in a dual lumen configuration. In one embodiment, as described above, the materials may be heat fused together at the mid-catheter joint 506. In another embodiment, a hypotube ring may be crimped around the mid-catheter joint 506. In yet another embodiment shown in FIG. 17B, the mid-catheter joint 550 may comprise a molded portion in order to consistently maintain co-axial distal annular lumens, a distal inflation lumen 552 and a distal guidewire lumen 554 (see cross-section 556 taken along A-A of FIG. 17B), a single proximal annular lumen, proximal inflation lumen 558, and an off-set dual lumen mid-catheter joint 550 (cross-section 560 taken along B-B of FIG. 17B), that includes a mid-catheter inflation lumen 562 and a mid-catheter guide wire lumen 564. This molded mid-joint connector allows for smooth advancement and retraction of balloon catheter 566 through the handle 102 described above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A method for treating a sinus opening, the method comprising:
   (a) transitioning a guide wire movement mechanism of a medical device from an unlocked configuration where a guide wire moves relative to the guide wire movement mechanism to a locked configuration where the guide wire cannot move relative to the guide wire movement mechanism, wherein the guide wire extends continuously through the guide wire movement mechanism in both the unlocked and locked configurations;
   (b) inserting the medical device partially into a patient's anatomy;
   (c) advancing the guide wire operatively extending from a rail of the medical device into the sinus opening of the patient by moving a linear actuator of the guide wire movement mechanism along a handle of the medical device;
   (d) rotating the guide wire in the locked configuration using a rotary actuator of the guide wire movement mechanism as the linear actuator remains slidably coupled with the handle;
   (e) advancing a balloon catheter of the medical device from an annular lumen of the medical device over both the rail and the guide wire by moving a balloon catheter movement mechanism along the handle of the medical device, wherein the annular lumen is disposed between the rail and a grooming sheath of the medical device; and
   (f) treating the sinus opening via inflation of the balloon catheter.

2. The method of claim 1, further comprising:
   (a) deflating the balloon catheter;
   (b) retracting the balloon catheter into the grooming sheath; and
   (c) removing the medical device from the patient's anatomy.

3. The method of claim 1, wherein the advancing includes advancing the guide wire from a rail lumen of the rail via a sliding movement of the guide wire movement mechanism of the medical device along the handle of the medical device.

4. The method of claim 3, further comprising:
   (a) deflating the balloon catheter;
   (b) retracting the balloon catheter into the grooming sheath and retracting the guide wire into the rail lumen; and
   (c) removing the medical device from the patient's anatomy.

5. The method of claim 1, wherein the patient's anatomy is a nostril.

6. The method of claim 1, wherein the rail is formed of a malleable material and the method further comprises configuring the malleable rail into a shape appropriate for the sinus opening to be treated prior to the inserting step.

7. The method of claim 1, wherein the treating step includes inflating a working segment of the balloon catheter that is disposed entirely over the guide wire.

8. The method of claim 1, wherein the treating step includes inflating a working segment of the balloon catheter that is disposed partially over the guide wire and partially over the rail.

9. The method of claim 1, wherein the treating step includes inflating a working portion of the balloon catheter that extends beyond a distal end of the guide wire.

10. The method of claim 1, further comprising suctioning the sinus opening.

11. The method of claim 1, further comprising irrigating the sinus opening.

12. The method of claim 1, wherein advancing the guide wire further comprises advancing the guide wire operatively extending from the rail of the medical device into the sinus opening of the patient by advancing an entirety of the guide wire movement mechanism that is coupled with the handle using a coupling portion.

13. A method for treating a sinus opening, the method comprising:
   (a) adjusting a length of a guide wire of a medical device extending distally beyond a guide wire movement mechanism of the medical device using the guide wire movement mechanism;
   (b) locking the guide wire movement mechanism by translating a rotary actuator of the guidewire movement mechanism relative to a linear actuator of the guidewire movement mechanism to prevent the guide wire from moving distally relative the guide wire movement mechanism, wherein the linear actuator includes proximal and distal ends that collectively confine translational movement of the rotary actuator;
   (c) inserting the medical device partially into a patient's anatomy;
   (d) driving the linear actuator of the guidewire movement mechanism along a handle guide portion of the medical device to advance the guide wire into the sinus opening of the patient;
   (e) advancing a balloon catheter of the medical device from an annular lumen of the medical device along both a rail of the medical device and the guide wire using a balloon catheter movement mechanism of the medical device, wherein the annular lumen is disposed between the rail and a grooming sheath of the medical device; and
   treating the sinus opening via inflation of the balloon catheter.

14. The method of claim 13, wherein the guide wire movement mechanism comprises an inner member and an outer member, wherein locking the guide wire movement mechanism further comprising coupling the inner member with the outer member to prevent the guide wire from moving distally relative the guide wire movement mechanism.

15. The method of claim 14, wherein the inner member includes a collet axle defined by the linear actuator, wherein the outer member includes a barrel defined by the rotary actuator, the method further comprising unlocking the guide wire movement mechanism prior to adjusting the length of the guide wire by moving the barrel in a first direction relative to the collet axle.

16. The method of claim 15, wherein the locking step further comprises locking the guide wire movement mechanism by moving the barrel in a second direction relative to the collet axle, wherein the second direction is opposite the first direction.

17. The method of claim 15, wherein the locking step further comprises locking a plurality of protrusions and slots of the collet axle onto the guide wire to rotatably couple the collet axle with the guide wire.

18. The method of claim 13, further comprising rotating the guide wire using the rotary actuator.

19. A method for treating a sinus opening, the method comprising:
   (a) adjusting a length of a guide wire of a medical device extending distally beyond a guide wire movement mechanism of the medical device using the guide wire movement mechanism by reducing a length of the guidewire that extends proximally beyond a guide wire movement mechanism;
   (b) locking the guide wire movement mechanism to prevent the guide wire from moving distally relative to the guide wire movement mechanism;
   (c) inserting the medical device partially into a patient's anatomy;
   (d) advancing the guide wire operatively extending from a rail of the medical device into the sinus opening of the patient;
   (e) rotating the guide wire using a rotary actuator of the guide wire movement mechanism as a linear actuator of the guide wire movement mechanism is slidably coupled with the handle;
   (f) advancing a balloon catheter of the medical device from an annular lumen of the medical device along both the rail of the medical device and the guide wire using a balloon catheter movement mechanism of the medical device, wherein the annular lumen is disposed between the rail and a grooming sheath of the medical device;
   (g) treating the sinus opening via inflation of the balloon catheter; and
   (h) at least partially collapsing the balloon catheter into the grooming sheath by retracting the balloon catheter relative to the grooming sheath.

20. The method of claim 19, further comprising deflating the balloon catheter prior to at least partially collapsing the balloon catheter into the grooming sheath.

* * * * *